(12) United States Patent
Malekkhosravi

(10) Patent No.: US 12,370,361 B2
(45) Date of Patent: Jul. 29, 2025

(54) MEDICAL LEAD RECONFIGURATION SYSTEM

(71) Applicant: Medtronic, Inc., Minneapolis, MN (US)

(72) Inventor: Shahram Malekkhosravi, Maple Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 462 days.

(21) Appl. No.: 17/805,312

(22) Filed: Jun. 3, 2022

(65) Prior Publication Data

US 2023/0001183 A1 Jan. 5, 2023

Related U.S. Application Data

(60) Provisional application No. 63/217,619, filed on Jul. 1, 2021.

(51) Int. Cl.
*A61N 1/05* (2006.01)
*A61N 1/36* (2006.01)
*A61N 1/372* (2006.01)

(52) U.S. Cl.
CPC ............ *A61N 1/05* (2013.01); *A61N 1/0534* (2013.01); *A61N 1/36132* (2013.01); *A61N 1/36185* (2013.01); *A61N 1/37247* (2013.01); *A61N 1/37252* (2013.01); *A61N 1/0551* (2013.01)

(58) Field of Classification Search
None
See application file for complete search history.

(56) References Cited

U.S. PATENT DOCUMENTS

| 5,824,030 A | 10/1998 | Yang et al. |
| 6,192,279 B1 | 2/2001 | Barreras, Sr. et al. |
| 7,212,867 B2 | 5/2007 | Van Venroo et al. |

(Continued)

OTHER PUBLICATIONS

Johnson et al., "Conceptual Design of Flex-DBS, a Mechanically Reconfigurable Deep Brain Stimulation Probe," Proceedings of the 2017 Design of Medical Devices Conference, DMD2017, Apr. 10-13, 2017, Minneapolis, Minnesota, USA, 2 pp.

(Continued)

*Primary Examiner* — Benjamin J Klein
*Assistant Examiner* — Luke M Stanley
(74) *Attorney, Agent, or Firm* — Shumaker & Sieffert, P.A.

(57) ABSTRACT

A medical device for electrical stimulation therapy including an implantable lead with multiple levels of lead electrodes in a first segmented electrode configuration, at least one level of the lead electrodes comprising segmented electrodes. A flexible member is configured to be disposed over the first electrode segmented electrode configuration, the flexible member having a first inner side and a first set of member electrodes, at least some of the first set of member electrodes configured to be positioned to electrically contact corresponding lead electrodes of the first segmented electrode configuration. The flexible member having a second outer side and a second set of member electrodes in a second segmented electrode configuration which is different than the first segmented electrode configuration, at least some of the second set of member electrodes electrically coupled to corresponding member electrodes of the first set of member electrodes.

22 Claims, 12 Drawing Sheets

(56) References Cited

U.S. PATENT DOCUMENTS

| | | | |
|---|---|---|---|
| 7,941,202 B2 | 5/2011 | Hetke et al. | |
| 8,340,783 B2 | 12/2012 | Sommer et al. | |
| 9,737,704 B2 | 8/2017 | Wahlstrand et al. | |
| 9,950,158 B2 | 4/2018 | True et al. | |
| 9,962,541 B2 | 5/2018 | Howard et al. | |
| 9,993,649 B2 | 6/2018 | Astrom et al. | |
| 10,463,265 B2 | 11/2019 | Bierbrauer et al. | |
| 2006/0282144 A1* | 12/2006 | Knapp | A61N 1/056 607/116 |
| 2008/0119711 A1* | 5/2008 | Nikumb | A61N 1/0534 600/378 |
| 2010/0042169 A1* | 2/2010 | Barker | H01R 13/639 607/2 |
| 2010/0331938 A1 | 12/2010 | Sommer et al. | |
| 2013/0013039 A1 | 1/2013 | Daglow et al. | |
| 2013/0204318 A1 | 8/2013 | Young | |
| 2013/0320273 A1* | 12/2013 | Kotov | A61B 5/24 423/447.2 |
| 2014/0172058 A1 | 6/2014 | Elahi et al. | |
| 2015/0328448 A1 | 11/2015 | Richter et al. | |
| 2017/0100580 A1* | 4/2017 | Olson | A61N 1/0551 |
| 2018/0333572 A1 | 11/2018 | Schuttler et al. | |
| 2019/0059820 A1 | 2/2019 | Schuettler et al. | |
| 2019/0143101 A1 | 5/2019 | Henle et al. | |
| 2019/0175917 A1 | 6/2019 | Lee | |
| 2019/0351219 A1 | 11/2019 | Mercanzini et al. | |
| 2020/0129757 A1* | 4/2020 | Xiao | A61B 5/374 |
| 2022/0361323 A1* | 11/2022 | Gardner | B33Y 80/00 |

OTHER PUBLICATIONS

Rossi et al., "Proceedings of the Third Annual Deep Brain Stimulation Think Tank: A Review of Emerging Issues and Technologies," Frontiers in Neuroscience, vol. 10, Article 119, doi: 10.3389/fnins.2016.00119, Apr. 2016, 15 pp.

Extended Search Report from counterpart European Application No. 22182629.0 dated Nov. 7, 2022, 5 pp.

Response to Communication pursuant to Rules 70(2) and 70a(2) EPC dated Nov. 3, 2022, from counterpart European Application No. 22182629, filed Jun. 16, 2023, 1 pp.

* cited by examiner

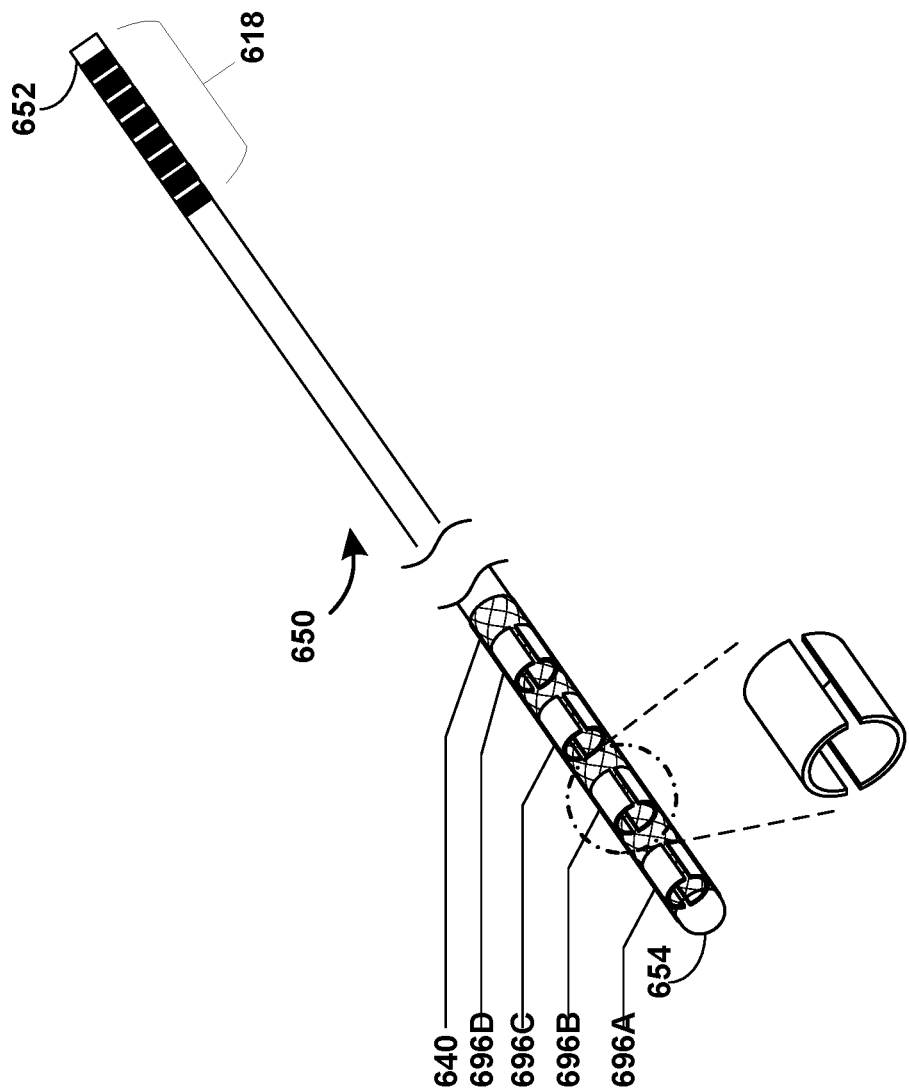

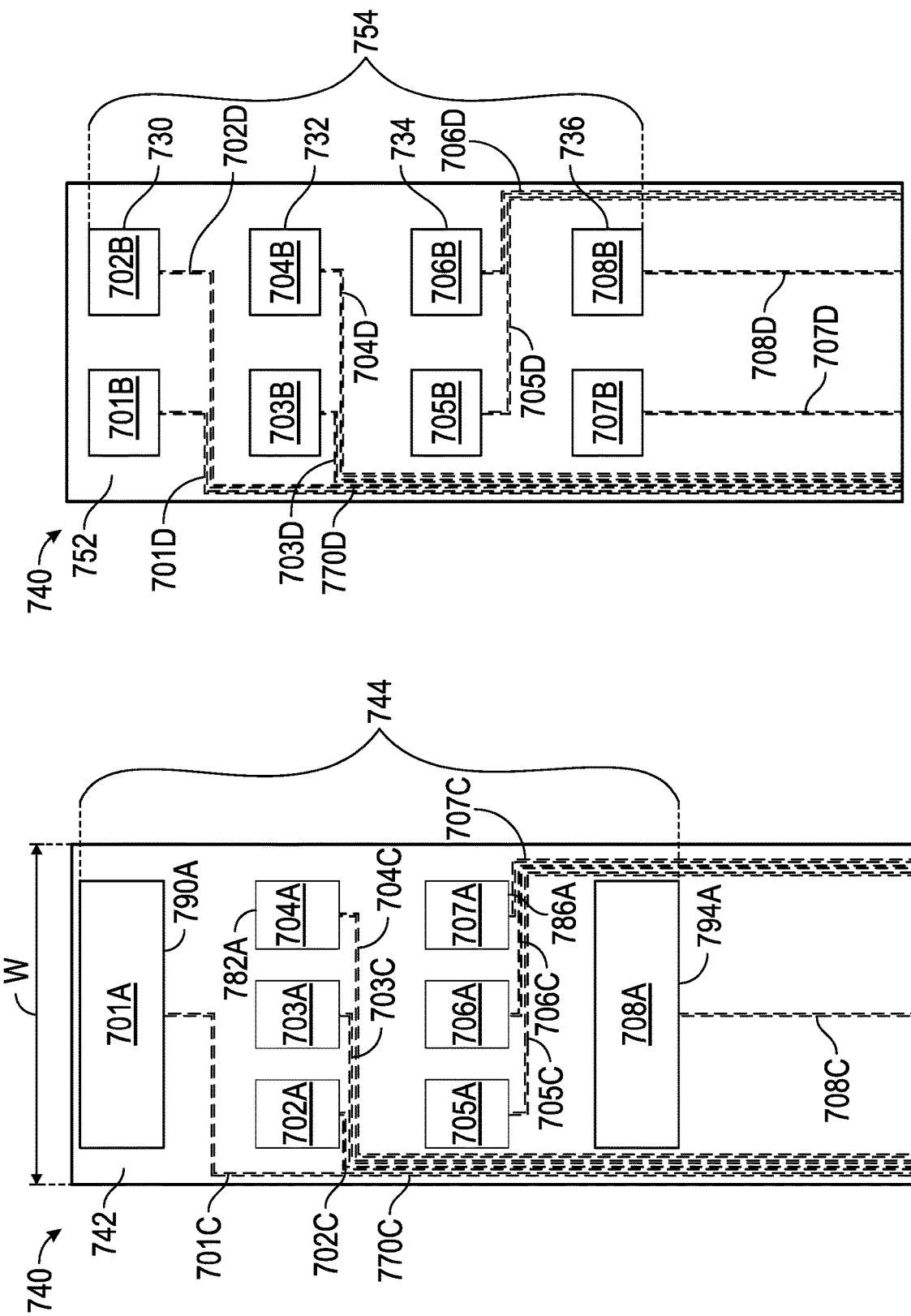

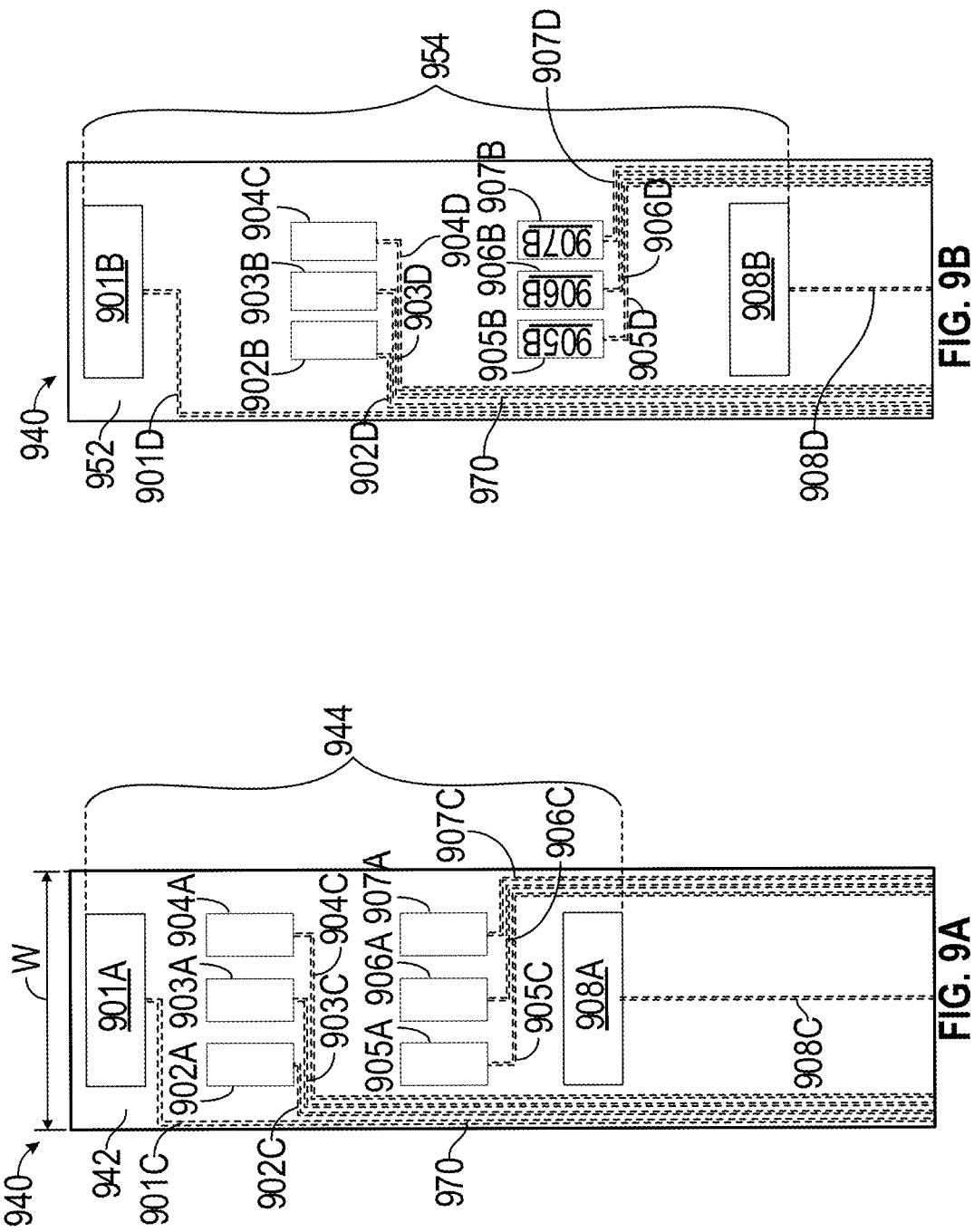

MEDICAL LEAD RECONFIGURATION SYSTEM

This application claims the benefit of U.S. Provisional Patent Application No. 63/217,619, filed Jul. 1, 2021, the entire content being incorporated herein by reference.

TECHNICAL FIELD

This disclosure relates to medical device systems including one or more reconfigurable leads.

BACKGROUND

Medical devices may be used to deliver therapy to a patient to treat symptoms or conditions such as chronic pain, seizure disorders (e.g., epilepsy), heart arrhythmias (e.g., fibrillation), tremor, Parkinson's disease, other types of movement disorders, obesity, mood disorders, urinary or fecal incontinence, or other types of symptoms or conditions. The therapy may be electrical stimulation therapy. Medical devices, such as implantable medical devices (IMDs), may be used for therapies such as deep brain stimulation (DBS), spinal cord stimulation (SCS), sacral neuromodulation, pelvic stimulation, gastric stimulation, peripheral nerve stimulation, cardiac stimulation, functional electrical stimulation, or other types of stimulation.

A medical device may include one or more leads carrying one or more electrodes. The medical device may deliver the electrical stimulation therapy to one or more target tissue sites within the patient and/or sense one or more electrical signals via the lead.

SUMMARY

The disclosed technology generally relates to reconfiguration of a lead of a medical device with electrodes arranged in an existing first electrode configuration to have electrodes arranged in a second electrode configuration.

A flexible member may be configured to be disposed over the first segmented electrode configuration of the lead, where the flexible member has a first inner side with a first set of member electrodes configured to be positioned to contact and be electrically coupled to corresponding electrodes of the existing first segmented electrode configuration. The flexible member may have a second outer side with a second set of member electrodes arranged in a second segmented electrode configuration which is different than the first segmented electrode configuration. The electrodes of the first inner side may be electrically coupled with corresponding electrodes of the second outer side. In some examples, the flexible member is a flexible circuit. In some examples, the flexible member has electrodes printed thereon, e.g., on the first and second outer sides. In some examples, the flexible member is disposed over, e.g., wrapped around, on the lead near the lead distal end or is a tube disposed over the lead. In some examples, at least some of the electrodes are segmented electrodes and/or at least one of the electrodes is a ring electrode.

In one or more examples, the existing first segmented electrode configuration for the segmented lead is for a 1-3-3-1 segmented lead, i.e., having a first ring electrode at a first axial level of the lead, three segmented electrodes at a second level, three segmented electrodes at a third level, and second ring electrode at a second level, and the second segmented electrode configuration is a 2-2-2-2 segmented lead, having first, second, third and fourth levels with two segmented electrodes each. In some examples, the existing first segmented electrode configuration for the segmented lead has the same number of electrodes as the second segmented electrode configuration. In other examples, the existing first segmented electrode configuration for the segmented lead includes a different number of electrodes than the second segmented electrode configuration.

In some examples, the disclosure describes a medical device for electrical stimulation therapy including an implantable lead with multiple levels of lead electrodes in a first segmented electrode configuration, at least one level of the lead electrodes comprising segmented electrodes. A flexible member is configured to be disposed over the first electrode segmented electrode configuration, the flexible member having a first inner side and a first set of member electrodes, at least some of the first set of member electrodes configured to be positioned to electrically contact corresponding lead electrodes of the first segmented electrode configuration. The flexible member may have a second outer side and a second set of member electrodes in a second segmented electrode configuration which is different than the first segmented electrode configuration, at least some of the second set of member electrodes electrically coupled to corresponding member electrodes of the first set of member electrodes.

In some examples, the disclosure describes a method includes placing a flexible member around an implantable lead, the implantable lead comprising multiple levels of lead electrodes in a first segmented electrode configuration, at least one level of electrodes comprising segmented electrodes, the flexible member having a first inner side and a first set of member electrodes mapped to the lead electrodes of the first segmented electrode configuration, and a second outer side having a second set of member electrodes in a second segmented electrode configuration which is different than the first segmented electrode configuration, wherein placing the flexible member around the implantable lead includes electrically coupling one or more of the first set of member electrodes with the lead electrodes and electrically coupling the lead electrodes with the second set of member electrodes.

The details of one or more aspects of the disclosure are set forth in the accompanying drawings and the description below. Other features, objects, and advantages will be apparent from the description and drawings, and from the claims.

BRIEF DESCRIPTION OF DRAWINGS

FIG. 6A is a conceptual diagram illustrating an example medical lead.

FIG. 7A is a conceptual diagram illustrating a first inner side of a flexible member in accordance with one or more techniques of this disclosure.

FIG. 7B is a conceptual diagram illustrating a second outer side of a flexible member in accordance with one or more techniques of this disclosure.

FIG. 9A is a conceptual diagram illustrating a first inner side of a flexible member in accordance with one or more techniques of this disclosure.

FIG. 9B is a conceptual diagram illustrating a second outer side of a flexible member in accordance with one or more techniques of this disclosure.

DETAILED DESCRIPTION

As described above, some examples of the disclosure relate to medical device leads (also referred to as "lead systems," "medical leads," or "leads") including one or more electrodes. Using the lead and electrode, a medical device may deliver or sense electrical signals to provide therapy to a patient to treat a patient condition. Medical leads may be fully implantable, percutaneously implantable, or external, and may include a distal conductive electrodes electrically and mechanically connected to one or more respective proximal electrodes, i.e., electrically conductive contacts, via one or more conductive lead wires (which also may be referred to as "conductors") extending through the lead body. Electrical stimulation from a medical device may be conducted along the lead wires to be delivered across the electrode surface. Likewise, signals sensed by the distal electrodes may be conducted along the lead wires to the proximal electrodes.

According to some techniques of the disclosure, distal electrodes and/or proximal electrodes (i.e., contacts) of a medical lead may be re-configured from a first electrode configuration to a second electrode configuration using a flexible member placed over the first electrode configuration. The flexible member may have a first inner side with a first set of electrodes configured to electrically contact corresponding lead electrodes of the first electrode configuration. The flexible member may have a second outer side and a second set of member electrodes in a second segmented electrode configuration which is different than the first segmented electrode configuration, and at least some of the second set of member electrodes may be electrically coupled to corresponding member electrodes of the first set of member electrodes. In some examples, the flexible member reconfigures the number of electrodes at each level. In some examples, the flexible member reconfigures spacing of the electrodes along the longitudinal axis of the lead. In some examples, the flexible member reconfigures the size of one or more electrodes. In some examples, the flexible member reconfigures the position of the electrodes.

Figure 1:
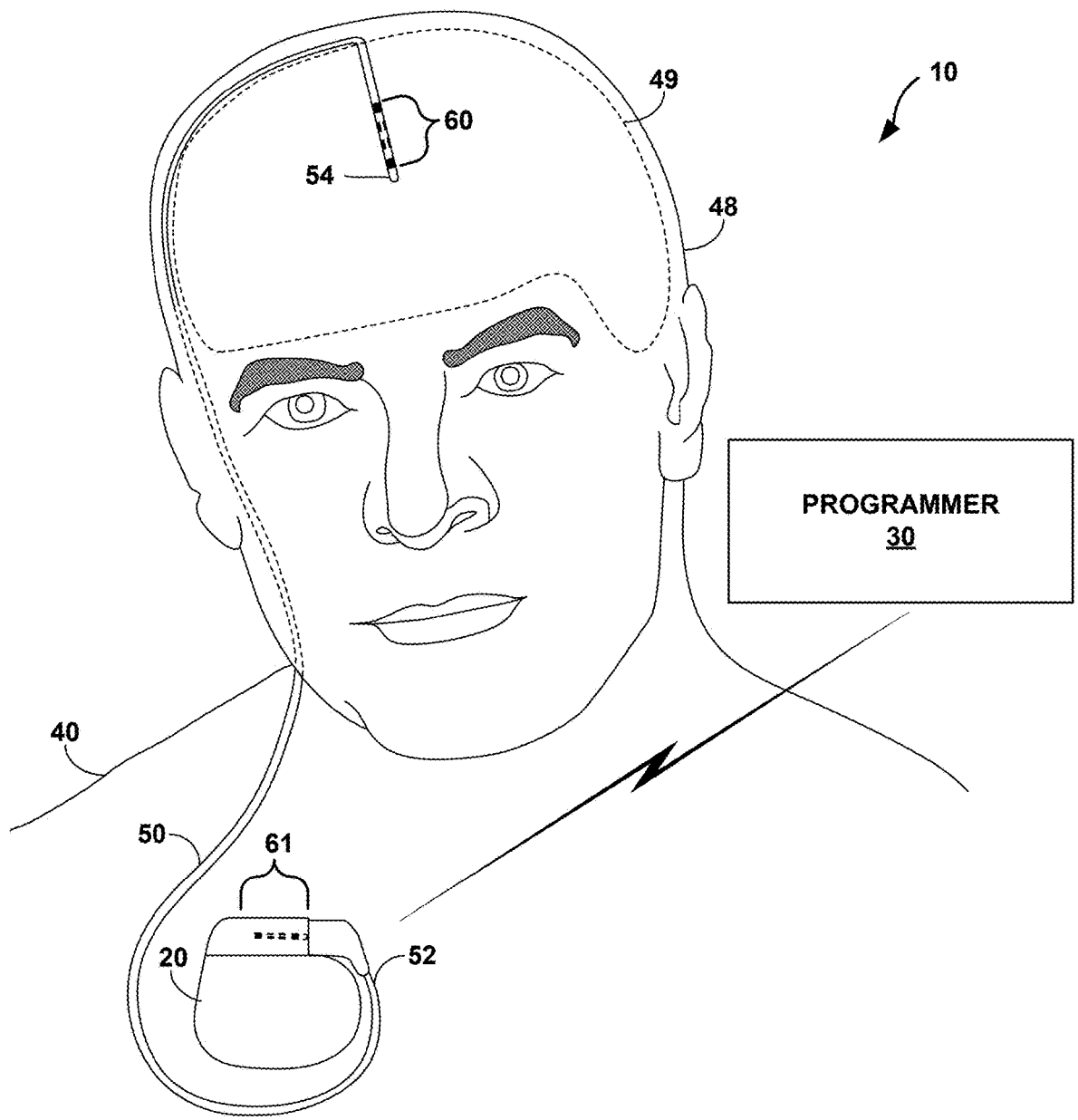
FIG. 1 is a conceptual diagram illustrating an example of a therapy system that delivers electrical stimulation therapy to a patient.

FIG. 1 is a conceptual diagram illustrating an exemplary therapy system 10 including lead 50 implanted in the brain 49 of patient 40. For ease of illustration, examples of the disclosure will primarily be described with regard to implantable electrical stimulation leads and implantable medical devices that apply neurostimulation therapy to brain 49 of patient 40 in the form of deep brain stimulation (DBS). However, the features and techniques described herein may be useful in other types of medical device systems which employ medical leads to deliver electrical stimulation to a patient and/or sense electrical signals via one or more electrodes of the lead, including other fully implantable leads, percutaneously implantable leads, or external leads. For example, the features and techniques described herein may be used in systems with medical devices that deliver stimulation therapy to a patient's heart, e.g., pacemakers, and pacemaker-cardioverter-defibrillators. As other examples, the features and techniques described herein may be embodied in systems that deliver other types of neurostimulation therapy (e.g., spinal cord stimulation, sacral nerve stimulation, peripheral nerve stimulation, or vagus nerve stimulation), stimulation of at least one muscle or muscle groups, stimulation of at least one organ such as gastric system stimulation, stimulation concomitant to gene therapy, and, in general, stimulation of any tissue of a patient. The medical lead system may be used with human subjects or with non-human subjects.

As shown in FIG. 1, therapy system 10 includes medical device programmer 30, implantable medical device (IMD) 20, and lead 50. In some examples, the therapy system 10 may include an external medical device. In some examples, the medical device may be an external trial stimulation, and the lead may be percutaneously implantable. Lead 50 includes plurality of electrodes 60 adjacent a distal end 54 of lead 50. IMD 20 includes a stimulation therapy module that includes an electrical stimulation generator that generates and delivers electrical stimulation therapy to one or more regions of brain 49 of patient 40 via one or more of electrodes 60. In the example shown in FIG. 1, therapy system 10 may be referred to as a DBS system because IMD 20 provides electrical stimulation therapy directly to tissue within brain 49, e.g., a tissue site under the dura mater of brain 49. In other examples, one or more of lead 50 may be positioned to deliver therapy to a surface of brain 49 (e.g., the cortical surface of brain 49).

In accordance with examples of the disclosure, lead 50 includes distal end 54 and a proximal end 52. In some examples, a flexible member (not shown in FIG. 1) is disposed over the lead 50 near the distal end 54 of the lead 50. Using conductive pathways within the lead and on or within the flexible member, IMD 20 may deliver electrical stimulation to patient 40 and/or sense electrical signals of patient 40 using lead 50. While FIG. 1 illustrates proximal end 52 of lead 50 connected directly to the header of IMD 20, in other examples, the proximal end of lead 50 may be connected to one or more lead extensions which are connected to the header of IMD 20 to electrically connect lead 50 to IMD 20.

In the example shown in FIG. 1, IMD 20 may be implanted within a subcutaneous pocket below the clavicle of patient 40. In other examples, IMD 20 may be implanted within other regions of patient 40, such as a subcutaneous pocket in the abdomen or buttocks of patient 40 or proximate the cranium 48 of patient 40. Proximal end 52 of lead 50 is coupled to IMD 20 via a connection sleeve block (also referred to as a header), which may include, for example, electrical contacts that electrically couple to respective electrical contacts at proximal end 52 of lead 50. The electrical contacts electrically couple the electrodes 60 carried by distal end 54 of lead 50. Lead 50 traverses from the implant site of IMD 20 within a chest cavity of patient 40, along the neck of patient 40 and through the cranium of patient 40 to access brain 49. Generally, IMD 20 is constructed of a biocompatible material that resists corrosion and degradation from bodily fluids. IMD 20 may comprise a hermetic housing to substantially enclose components, such as a processor, therapy module, and memory.

Lead 50 may be positioned to deliver electrical stimulation to one or more target tissue sites within brain 49 to manage patient symptoms associated with a disorder of patient 40. Lead 50 may be implanted to position electrodes 60 at desired locations of brain 49 through respective holes in cranium 48. Lead 50 may be placed at any location within brain 49 such that electrodes 60 are capable of providing electrical stimulation to target tissue sites within brain 49 during treatment. Although FIG. 1 illustrates system 10 as including a single lead 50 coupled to IMD 20, in some examples, system 10 may include more than one lead, including leads positioned in different regions of the body, such as in different hemispheres of the brain or at different positions within the epidural space of the spinal cord.

Lead 50 may deliver electrical stimulation via electrodes 60 to treat any number of neurological disorders or diseases in addition to movement disorders, such as seizure disorders or psychiatric disorders. Lead 50 may be implanted within a desired location of brain 49 via any suitable technique, such as through respective burr holes in a skull of patient 40 or through a common burr hole in the cranium 48. Lead 50 may be placed at any location within brain 49 such that electrodes 60 of lead 50 are capable of providing electrical stimulation to targeted tissue during treatment. In the examples shown in FIG. 1, electrodes 60 of lead 50 are shown as segmented electrodes and ring electrodes. In some examples, at least one electrode of electrodes 60 is a ring electrode. In some examples, electrodes 60 are each ring electrodes. In some examples, at least one electrode of electrodes 60 is a segmented electrode. In some examples, electrodes 60 are each segmented electrodes. In some examples, lead 50 includes one or more ring electrodes and a plurality of segmented electrodes. Electrodes 60 of lead 50 may have a complex electrode array geometry that is capable of producing shaped electrical fields. In this manner, electrical stimulation may be directed to a specific direction from lead 50 to enhance therapy efficacy and reduce possible adverse side effects from stimulating a large volume of tissue.

IMD 20 may deliver electrical stimulation therapy to brain 49 of patient 40 according to one or more stimulation therapy programs. A therapy program may define one or more electrical stimulation parameter values for therapy generated and delivered from IMD 20 to brain 49 of patient 40. Where IMD 20 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy may be further characterized by different electrode combinations, which can include selected electrodes and their respective polarities. The exact therapy parameter values of the stimulation therapy that helps manage or treat a patient disorder may be specific for the particular target stimulation site (e.g., the region of the brain) involved as well as the particular patient and patient condition.

In addition to delivering therapy to manage a disorder of patient 40, therapy system 10 monitors electrical signals, such as, e.g., one or more bioelectrical brain signals of patient 40. For example, IMD 20 may include a sensing module that senses bioelectrical brain signals within one or more regions of brain 49. In the example shown in FIG. 1, the signals generated by electrodes 60 are conducted to the sensing module within IMD 20 via conductors within lead 50, including one or more conductors within lead 50 extending between distal electrodes 60 at distal end 54 and proximal electrodes (i.e., contacts) at proximal end 52 of lead 50.

Programmer 30 wirelessly communicates with IMD 20 as needed to provide or retrieve therapy information. Programmer 30 is an external computing device that the user, e.g., the clinician and/or patient 40, may use to communicate with IMD 20. For example, programmer 30 may be a clinician programmer that the clinician uses to communicate with IMD 20 and program one or more therapy programs for IMD 20. Alternatively, programmer 30 may be a patient programmer that allows patient 40 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 20.

Programmer 30 may be a hand-held computing device with a display viewable by the user and an interface for providing input to programmer 30 (i.e., a user input mechanism). In other examples, programmer 30 may be a larger workstation or a separate application within another multi-function device, rather than a dedicated computing device. For example, the multi-function device may be a notebook computer, tablet computer, workstation, cellular phone, personal digital assistant, or another computing device that may run an application that enables the computing device to operate as a secure medical device programmer 30.

Again, while lead 50 is described here for use in DBS applications, lead 50 or other leads may be implanted at any other location within patient 40. For example, lead 50 may be implanted near the spinal cord, pudendal nerve, sacral nerve, or any other nervous or muscle tissue that may be stimulated. The user interface described herein may be used to program the stimulation parameters of any type of stimulation therapy. In the case of pelvic nerves, defining a stimulation field may allow the clinician to stimulate multiple desired nerves without placing multiple leads deep into patient 40 and adjacent to sensitive nerve tissue. Therapy may also be changed if leads migrate to new locations within the tissue or patient 40 no longer perceives therapeutic effects of the stimulation. The features or techniques of this disclosure may be useful in other types of medical applications.

Figure 2:
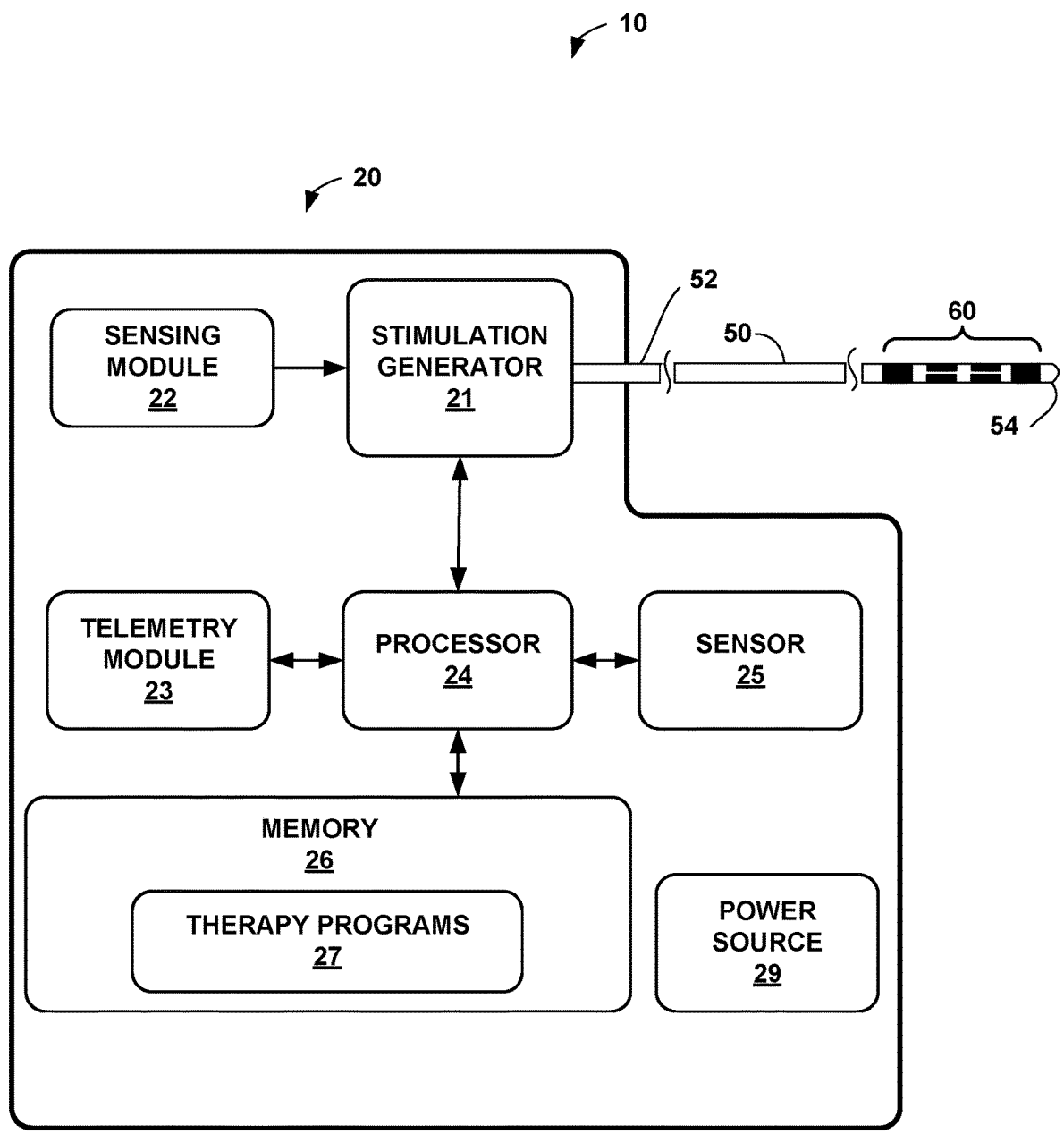
FIG. 2 is a conceptual block diagram of an example of a medical device system.

FIG. 2 is a functional block diagram illustrating components of IMD 20. As shown, therapy system 10 includes IMD 20 coupled to lead 50. In the example of FIG. 2, IMD 20 includes processor circuitry 24 (also referred to as "processor"), memory 26, stimulation generator 21, sensing module 22, telemetry module 23, sensor 25, and power source 29. Each of these components (also referred to as "modules" may be or include electrical circuitry configured to perform the functions attributed to each respective module). For example, processor 24 may include processing circuitry, stimulation generator 21 may include switch circuitry, sensing module 22 may include sensing circuitry, and telemetry module 23 may include telemetry circuitry. Memory 26 may include any volatile or non-volatile media, such as a random-access memory (RAM), read only memory (ROM), non-volatile RAM (NVRAM), electrically erasable programmable ROM (EEPROM), flash memory, and the like. Memory 26 may store computer-readable instructions that, when executed by processor 24, cause IMD 20 to perform various functions. Memory 26 may be a storage device or other non-transitory medium.

Processor 24 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processor 24 herein may be embodied as firmware, hardware, software or any combination thereof. Processor 24 controls stimulation generator 21 to apply particular stimulation parameter values, such as amplitude, pulse width, and pulse rate.

In the example shown in FIG. 2, lead 50 includes electrodes 60 located at distal end 54. Processor 24 also controls stimulation generator 21 to generate and apply the stimulation signals to selected combinations of electrodes of the electrode module. In some examples, stimulation generator 21 includes a switch module that couples stimulation signals to selected conductors within lead 50, which, in turn, delivers the stimulation signals across selected electrodes. Such a switch module may be a switch array, switch matrix, multiplexer, or any other type of switching module configured to selectively couple stimulation energy to selected electrodes and to selectively sense bioelectrical neural signals of the spine with selected electrodes.

In other examples, however, stimulation generator 21 does not include a switch module. In these examples, stimulation generator 21 comprises a plurality of pairs of voltage sources, current sources, voltage sinks, or current sinks connected to each of electrodes such that each pair of electrodes has a unique signal generator. In other words, in these examples, each of electrodes 60 is independently controlled via its own signal generator (e.g., via a combination of a regulated voltage source and sink or regulated current source and sink), as opposed to switching signals between electrodes.

Stimulation generator 21 may be a single channel or multi-channel stimulation generator. In particular, stimulation generator 21 may be capable of delivering a single stimulation pulse or multiple stimulation pulses at a given time via a single electrode combination or multiple stimulation pulses at a given time via multiple electrode combinations. In some examples, however, stimulation generator 21 may be configured to deliver multiple channels on a time-interleaved basis. For example, a switch module of stimulation generator 21 may serve to time divide the output of stimulation generator 21 across different electrode combinations at different times to deliver multiple programs or channels of stimulation energy to patient 40. In another example, the stimulation generator 21 may control the independent sources or sinks on a time-interleaved bases.

Lead 50 may include distal end 54 including a complex electrode array geometry, but may also include one or more single ring electrodes along the longitudinal axis in other examples. In one example, distal end 54 of lead 50 includes a plurality of electrodes 60 positioned at different axial positions along the longitudinal axis of the lead and a plurality of electrodes 60 positioned at different angular positions around the circumference of the lead (which may be referred to as electrode segments). In this manner, electrodes may be selected along the longitudinal axis of lead 50 and along the circumference of the lead. Selectively activating electrodes 60 of lead 50 can produce customizable stimulation fields that may be directed to a particular side of lead 50 in order to isolate the stimulation field around the target anatomical region of brain 49.

Although sensing module 22 is incorporated into a common housing with stimulation generator 21 and processor 24 in FIG. 2, in other examples, sensing module 22 may be in a separate housing from IMD 20 and may communicate with processor 24 via wired or wireless communication techniques. Example bioelectrical signals include, but are not limited to, local field potentials (LFPs), evoked compound action potentials (ECAPs), or other signals within one or more regions of the spine or brain, for example.

Sensor 25 may include one or more sensing elements that sense values of a respective patient parameter. For example, sensor 25 may include one or more accelerometers, optical sensors, chemical sensors, temperature sensors, pressure sensors, or any other types of sensors. Sensor 25 may output patient parameter values that may be used as feedback to control delivery of therapy. IMD 20 may include additional sensors within the housing of IMD 20 and/or coupled as a separate module via one of lead 50 or other leads. In addition, IMD 20 may receive sensor signals wirelessly from remote sensors via telemetry module 23, for example. In some examples, one or more of these remote sensors may be external to patient (e.g., carried on the external surface of the skin, attached to clothing, or otherwise positioned external to the patient).

Telemetry module 23 supports wireless communication between IMD 20 and an external programmer (e.g., such as programmer 30) or another computing device under the control of processor 24. Processor 24 of IMD 20 may receive, as updates to programs, values for various stimulation parameters such as amplitude and electrode combination, from programmer 30 via telemetry module 23. The updates to the therapy programs may be stored within therapy programs 27 portion of memory 26. Telemetry module 23 in IMD 20, as well as telemetry modules in other devices and systems described herein, such as programmer 30, may accomplish communication by radiofrequency (RF) communication techniques. In addition, telemetry module 23 may communicate with external medical device programmer 30 via proximal inductive interaction of IMD 20 with programmer 30. Accordingly, telemetry module 23 may send information to programmer 30 on a continuous basis, at periodic intervals, or upon request from IMD 20 or programmer 30.

Power source 29 delivers operating power to various components of IMD 20. Power source 29 may include a small rechargeable or non-rechargeable battery and a power generation circuit to produce the operating power. Recharging may be accomplished through proximal inductive interaction between an external charger and an inductive charging coil within IMD 20. In some examples, power requirements may be small enough to allow IMD 20 to utilize patient motion and implement a kinetic energy-scavenging device to trickle charge a rechargeable battery. In other examples, traditional batteries may be used for a limited period of time.

Figure 3A:
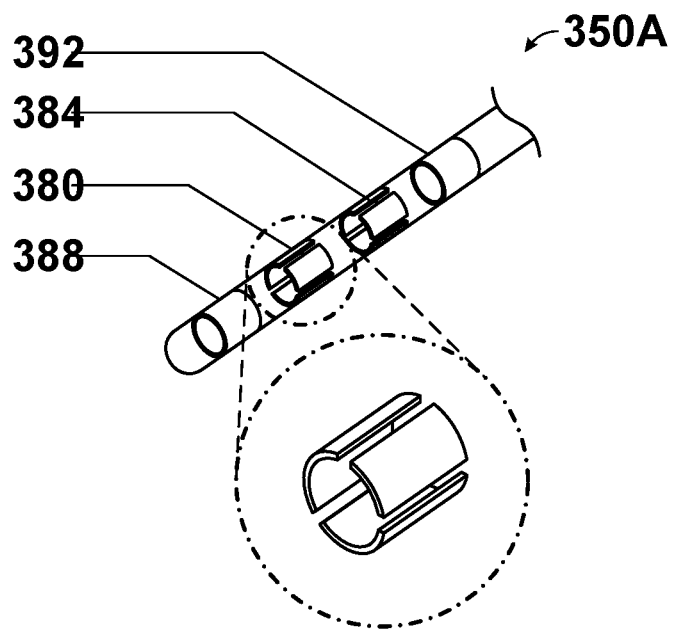
FIG. 3A is a conceptual diagram illustrating a distal end of an example conductor assembly for a medical lead.
Figure 4A:
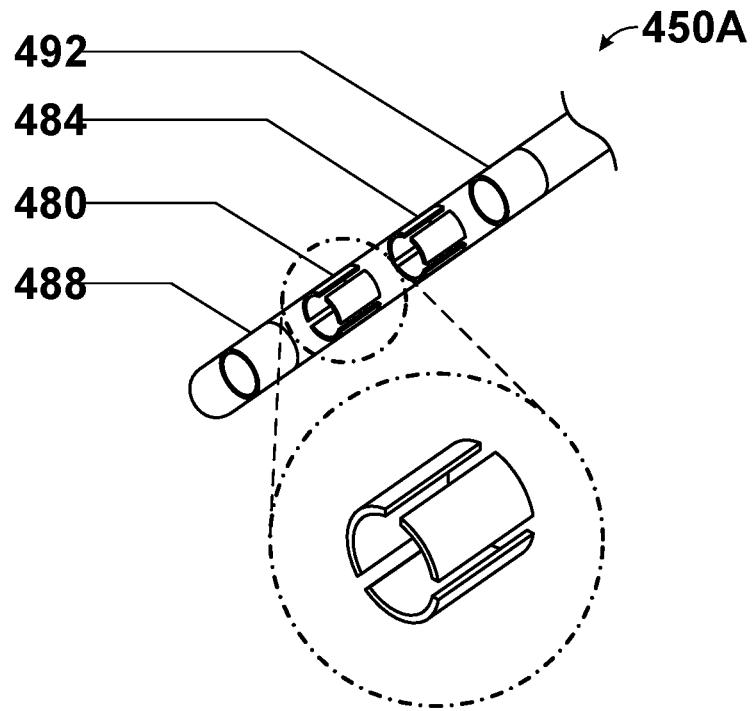
FIG. 4A is a conceptual diagram illustrating a distal end of an example conductor assembly for a medical lead.
Figure 5A:
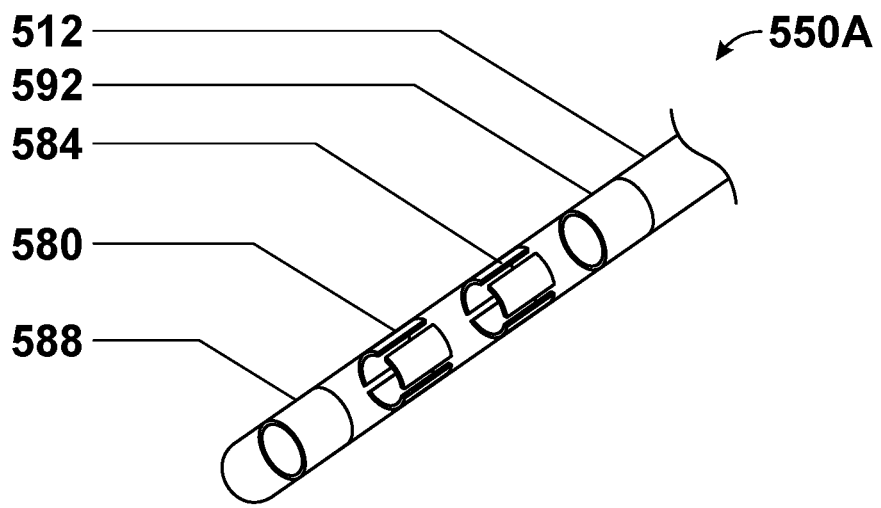
FIG. 5A is a conceptual diagram illustrating a distal end of an example conductor assembly for a medical lead.

FIGS. 3A, 4A, and 5A illustrate example leads 350, 450, 550 (collectively, leads 50), which may have various lead configurations including various types of electrodes and various longitudinal spacing of electrodes In some examples leads 50 include two ring electrodes with two segmented electrode rings each having three segmented electrodes (e.g., segmented electrodes) although the techniques described herein may be applied to leads having more or fewer segmented electrodes within a segmented electrode ring and/or to leads having more or fewer than two segmented electrode rings. These techniques may also be applied to leads having more or fewer than two ring electrodes. In yet other cases, lead 50 may include only segmented electrodes or only ring electrodes.

Figure 3B:
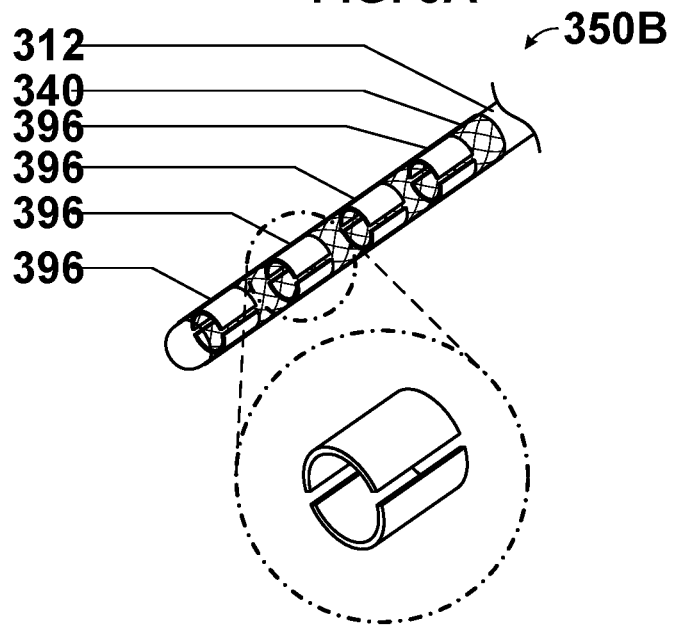
FIG. 3B is a conceptual diagram illustrating a distal end of an example conductor assembly for a medical lead.

FIGS. 3A and 3B are conceptual diagrams illustrating an example of a distal end portion of medical lead 350, where FIG. 3A illustrates a lead 350A with a first segmented electrode configuration, and FIG. 3B illustrates a lead 350B with a second segmented electrode configuration, where FIG. 3B illustrates the lead of FIG. 3A with a flexible member 340 disposed on the lead 350 to reconfigure the electrodes. In the example of FIG. 3A, lead 350 represents a lead having a first configuration of 1-3-3-1 including a first ring electrode 388, a first level of three segmented electrodes 380, a second level of three segmented electrodes 384, and a second ring electrode 392. FIG. 3B illustrates a lead 350B which has been re-configured, with a flexible member, to a second configuration of 2-2-2-2, where each level includes two segmented electrodes 396. The first and second electrode configurations may have the same number of electrodes, e.g., 8 in the example of FIGS. 3A and 3B. In some examples, the first and second electrode configurations may have 16 electrodes. In other examples, the first and second electrode configurations may have different numbers of electrodes. For example, the first segmented electrode configuration may have more or less electrodes than the second segmented electrode configuration.

To achieve a second configuration, a flexible member 340 is disposed over at least a portion of the lead 350A such that at least some of a first set of member electrodes (FIG. 7A) on a first, inner side of the flexible member may be positioned to electrically contact corresponding lead electrodes 388, 380, 384, 392 of the first segmented electrode configuration of the lead. A second set of member electrodes on a second outer side of flexible member 340 may have electrodes that are arranged in a second electrode configuration, different than the first electrode configuration, and electrically coupled to corresponding electrodes in the first set of member electrodes, resulting in lead 350B having an electrode configuration different than that of lead 350A (i.e., a second 2-2-2-2 electrode configuration provided by the second set of member electrodes of flexible member 340 on lead 350B rather than a first 1-3-3-1 configuration provided by the lead electrodes 388, 380, 384, 392 on lead 350A).

In some examples, the flexible member 340 is wrapped around only a portion of the lead 350. In some examples, the flexible member 340 is wrapped fully around a circumference of the lead 350. In some examples, the flexible member 340 is wrapped around the lead 350 such that the flexible member 340 at least partially overlaps itself around the lead. In some examples, the flexible member 340 may be a partial section that extends axially over the electrodes or at least some of the electrodes. In some examples, the flexible member extends axially over the electrodes or at least some of the electrodes but not the entire lead. In some examples, the flexible member may be a wrapped band or a tube that is open at both ends to leave a portion of the lead, such as the distal tip, exposed. In some examples, the flexible member may be a wrapped band or a tube that is open at one end to cover an end of the lead.

The flexible member 340 has a second set of member electrodes 354 in a second segmented electrode configuration which is different than the first segmented electrode configuration. At least some of the second set of member electrodes 354, for example, the two segmented electrodes 396, are electrically coupled to corresponding member electrodes of the first set of member electrodes, and the lead electrodes 388, 380, 384, 392 are thereby electrically coupled with the second set of member electrodes 354, albeit in a different configuration than the first configuration.

Lead 350 may include a lead body 312 extending between distal end 54 and proximal end 52 (FIG. 1). For the purposes of illustration of the electrodes, lead body 312 is shown translucent. Lead 350 may further include one or more proximal electrodes 61 near the proximal end 52, where the proximal electrodes may be electrically coupled to the lead electrodes 388, 380, 384, 392 near the distal end of the lead via conductors that extend within lead body 312. The proximal electrodes 61 may be configured to electrically couple with respective terminals of IMD 20 of FIG. 1, to therapy connect proximal electrodes 61 and lead electrodes 388, 380, 384, 392 to circuitry with in IMD 20. In some examples, at least one of the proximal electrodes 61 may be electrically coupled via the flexible member 340 and a lead conductor to one or more of the second set of member electrodes, for example, to the two segmented electrodes 396.

Figure 4B:
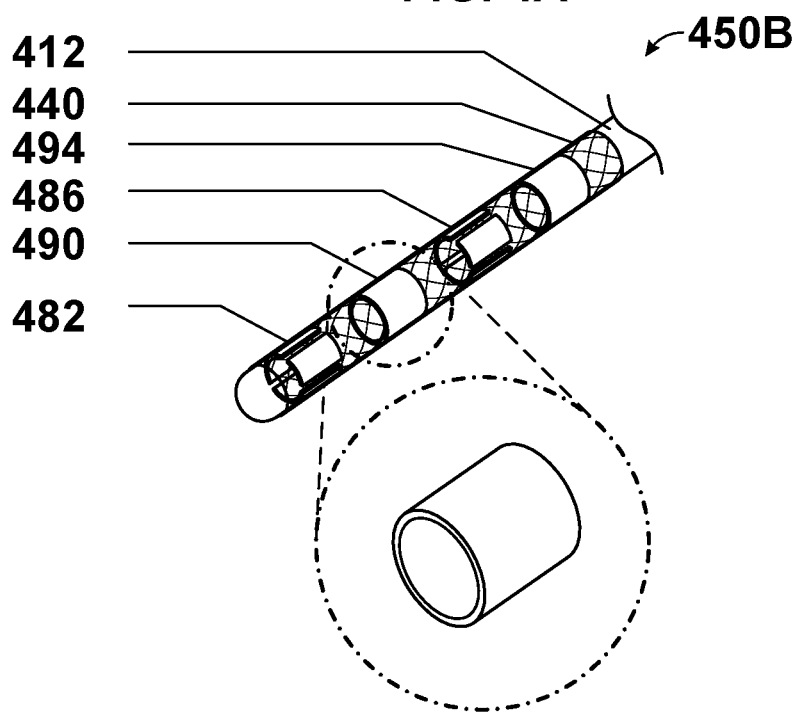
FIG. 4B is a conceptual diagram illustrating a distal end of an example conductor assembly for a medical lead.

FIGS. 4A and 4B are conceptual diagrams illustrating another example of a distal end portion of medical lead 450, where FIG. 4A illustrates a lead 450A with a first segmented electrode configuration, and FIG. 4B illustrates a lead 450B with a second segmented electrode configuration where FIG. 4B illustrates the lead of FIG. 4A with a flexible member disposed on the lead to reconfigure the electrodes. In the example of FIG. 4A, lead 450 represents a lead having a first configuration of 1-3-3-1 including a first ring electrode 488, a first level of three segmented electrodes 480, a second level of three segmented electrodes 484, and a second ring electrode 492. FIG. 4B illustrates a lead 450B which has been re-configured, with addition of a flexible member, to a second configuration of 3-1-3-1, including a member second outer side first level of three segmented electrodes 482, a member second outer side first ring electrode 490, a member second outer side second level of three segmented electrodes 486, and a member second outer side second ring electrode 494. The first and second electrode configurations may have the same number of electrodes, e.g., 8 in the example of FIGS. 4A and 4B. In other examples, the first and second electrode configurations may have different numbers of electrodes. For example, the first segmented electrode configuration may have more or less electrodes than the second segmented electrode configuration.

To achieve a second configuration, a flexible member 440 is disposed over at least a portion of the lead 450A such that at least some of a first set of member electrodes (FIG. 6) on a first, inner side of the flexible member may be positioned to electrically contact corresponding lead electrodes 488, 480, 484, 492 of the first segmented electrode configuration of the lead. A second set of member electrodes on a second outer side of flexible member 440 may have electrodes that are arranged in a second electrode configuration, different than the first electrode configuration, and electrically coupled to corresponding electrodes in the first set of member electrodes, resulting in lead 450B having an electrode configuration different than that of lead 450A (i.e., a 3-1-3-1 electrode configuration formed by the second set of member electrodes 482, 490, 486, 494 of flexible member 440 rather than an original 1-3-3-1 configuration formed by lead electrodes 488, 480, 484, 492 without the flexible member).

In some examples, the flexible member 440 is wrapped around only a portion of the lead 450. In some examples, the flexible member 440 is wrapped fully around a circumference of the lead 450. In some examples, the flexible member 440 is wrapped around the lead 450 such that the flexible member 440 at least partially overlaps itself around the lead. In some examples, the flexible member 440 may be a partial section that extends axially over the electrodes or at least some of the electrodes. In some examples, the flexible member extends axially over the electrodes or at least some of the electrodes but not the entire lead. In some examples, the flexible member may be a wrapped band or a tube that is open at both ends to leave a portion of the lead, such as the distal tip, exposed. In some examples, the flexible member may be a wrapped band or a tube that is open at one end to cover an end of the lead.

The flexible member 440 has a second set of member electrodes 454 in a second segmented electrode configuration which is different than the first segmented electrode configuration. At least some of the second set of member electrodes 454, for example, the two segmented electrodes 496, are electrically coupled to corresponding member electrodes of the first set of member electrodes, and the lead electrodes 488, 480, 484, 492 are thereby electrically coupled with the second set of member electrodes 482, 490, 486, 494, albeit in a different configuration than the first configuration.

Lead 450 may include a lead body 412 extending between distal end 54 and proximal end 52 (FIG. 1). For the purposes of illustration of the electrodes, lead body 412 is shown translucent. Lead 450 may further include one or more proximal electrodes 61 near the proximal end 52, where the proximal electrodes may be electrically coupled to the lead electrodes 488, 480, 484, 492 near the distal end of the lead via conductors that extend within lead body 412. The proximal electrodes 61 may be configured to electrically couple with respective terminals of IMD 20 of FIG. 1, to therapy connect proximal electrodes 61 and lead electrodes 488, 480, 484, 492 to stimulation and/or sensing circuitry within IMD 20. In some examples, at least one of the proximal electrodes 61 may be electrically coupled via the flexible member 440 and a lead conductor to one or more of to the second set of member electrodes 482, 490, 486, 494.

Figure 5B:
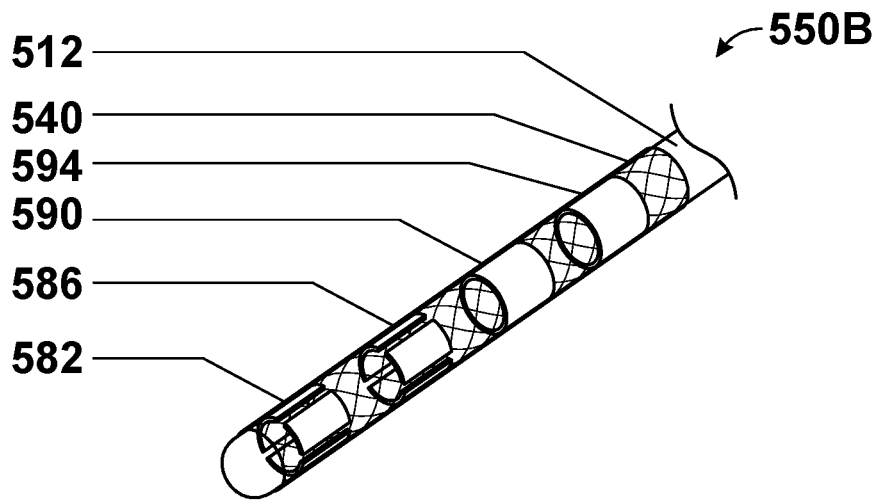
FIG. 5B is a conceptual diagram illustrating a distal end of an example conductor assembly for a medical lead.

FIGS. 5A and 5B are conceptual diagrams illustrating another example of a distal end portion of medical lead 550, where FIG. 5A illustrates a lead 550A with a first segmented electrode configuration, and FIG. 5B illustrates a lead 550B with a second segmented electrode configuration where FIG. 5B illustrates the lead of FIG. 5A with a flexible member disposed on the lead to reconfigure the electrodes. In the example of FIG. 5A, lead 550 represents a lead having a first configuration of 1-3-3-1 including a first ring electrode 588, a first level of three segmented electrodes 580, a second level of three segmented electrodes 584, and a second ring electrode 592. FIG. 5B illustrates a lead 550B which has been re-configured to a second configuration of 3-3-1-1, including a member second outer side first level of three segmented electrodes 582, a member second outer side second level of three segmented electrodes 586, a member second outer side first ring electrode 590, and a member second outer side second ring electrode 594. The first and second electrode configurations may have the same number of electrodes, e.g., 8 in the example of FIGS. 5A and 5B. In other examples, the first and second electrode configurations may have different numbers of electrodes. For example, the first segmented electrode configuration may have more or less electrodes than the second segmented electrode configuration.

To achieve a second configuration, a flexible member 540 is disposed over at least a portion of the lead 550A such that at least some of a first set of member electrodes (FIG. 10A) on a first, inner side of the flexible member 540 may be positioned to electrically contact corresponding lead electrodes 588, 580, 584, 592 of the first segmented electrode configuration of the lead. A second set of member electrodes on a second outer side of flexible member 540 may have electrodes that are arranged in a second electrode configuration, different than the first electrode configuration, and electrically coupled to corresponding electrodes in the first set of member electrodes, resulting in lead 550B having an electrode configuration different than that of lead 550A (i.e., a second 3-3-1-1 electrode configuration provided by the second set of member electrodes of flexible member 540 on lead 550B rather than a first 1-3-3-1 configuration provided by the lead electrodes 588, 580, 584, 592 on lead 550A).

In some examples, the flexible member 540 is wrapped around only a portion of the lead 550. In some examples, the flexible member 540 is wrapped fully around a circumference of the lead 550. In some examples, the flexible member 540 is wrapped around the lead 550 such that the flexible member 540 at least partially overlaps itself around the lead. In some examples, the flexible member 540 may be a partial section that extends axially over the electrodes or at least some of the electrodes. In some examples, the flexible member extends axially over the electrodes or at least some of the electrodes but not the entire lead. In some examples, the flexible member may be a wrapped band or a tube that is open at both ends to leave a portion of the lead, such as the distal tip, exposed. In some examples, the flexible member may be a wrapped band or a tube that is open at one end to cover an end of the lead.

The flexible member 540 has a second set of member electrodes 554 in a second segmented electrode configuration which is different than the first segmented electrode configuration. At least some of the second set of member electrodes 554, for example, the two segmented electrodes 596, are electrically coupled to corresponding member electrodes of the first set of member electrodes, and the lead electrodes 588, 580, 584, 592 are thereby electrically coupled with the second set of member electrodes 554, albeit in a different configuration than the first configuration.

Lead 550 may include a lead body 512 extending between distal end 54 and proximal end 52 (FIG. 1). For the purposes of illustration of the electrodes, lead body 512 is shown translucent. Lead 550 may further include one or more proximal electrodes 61 near the proximal end 52, where the proximal electrodes may be electrically coupled to the lead electrodes 588, 580, 584, 592 near the distal end of the lead via conductors that extend within lead body 512. The proximal electrodes 61 may be configured to electrically couple with respective terminals of IMD 20 of FIG. 1, to therapy connect proximal electrodes 61 and lead electrodes 588, 580, 584, 592 to circuitry within IMD 20. In some examples, at least one of the proximal electrodes 61 may be electrically coupled via the flexible member 540 and a lead conductor to one or more of the second set of member electrodes, for example, to the two segmented electrodes 596.

FIG. 6A is a conceptual of a lead 650 with the flexible member 640 installed thereon. Lead 650 extends from a proximal end 652 to a distal end 654, where the flexible member 640 may be disposed near the distal end 654 of the lead 650. In some examples, the flexible member 440 may be a partial section that extends axially over the electrodes or at least some of the electrodes. In some examples, the flexible member extends axially over the electrodes or at least some of the electrodes but not the entire lead. In some examples, the flexible member may be a wrapped band or a tube that is open at both ends to leave a portion of the lead, such as the distal tip, exposed. In some examples, the flexible member may be a wrapped band or a tube that is open at one end to cover an end of the lead.

Figure 6B:
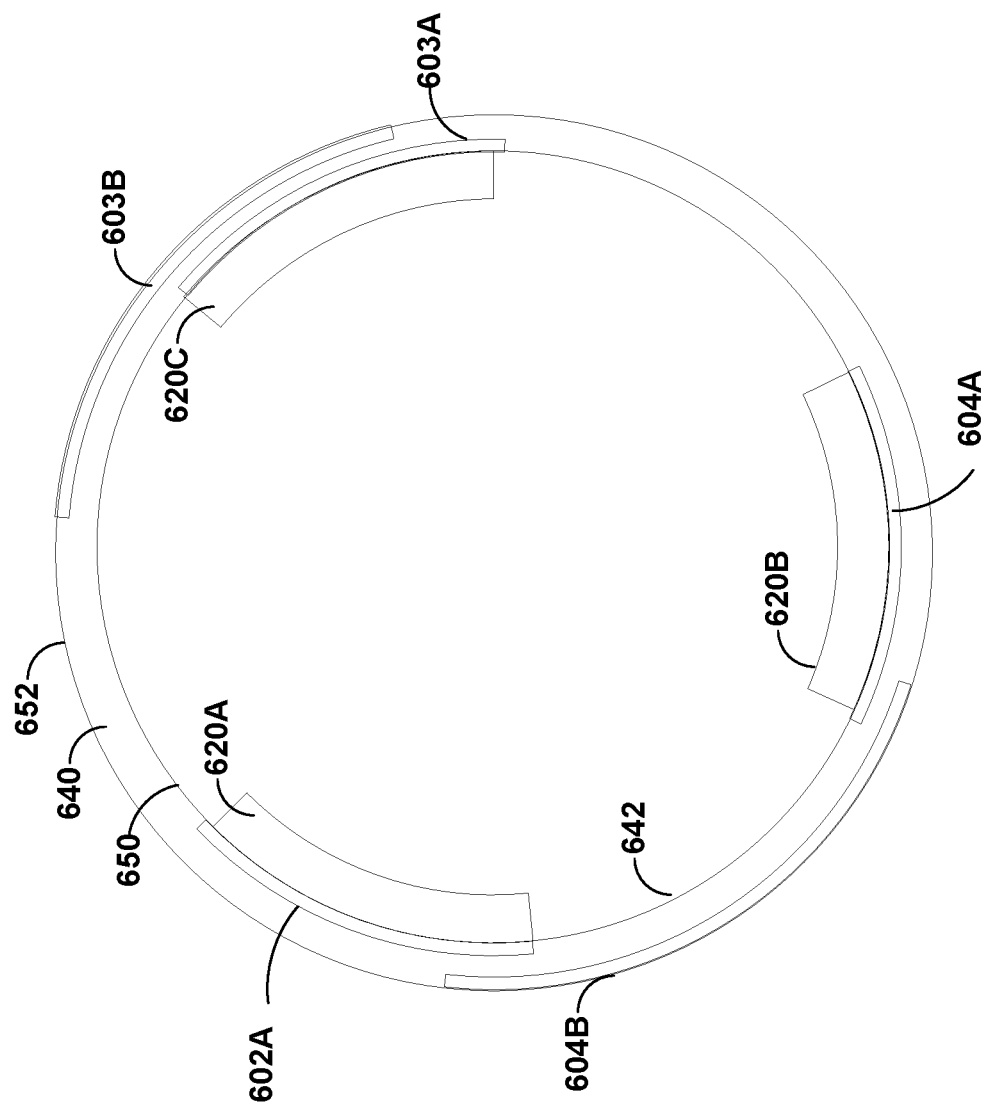
FIG. 6B is a cross-sectional view illustrating a cross-section near a distal end of an example conductor assembly for a medical lead.

As discussed above, flexible member 640 includes a second set of member electrodes 696A, 696B, 696C, 696D that may be electrically coupled with a first set of member electrodes (FIG. 6B) disposed on an inner side of the flexible member 640, and the first set of member electrodes may be electrically coupled with the distal lead electrodes (FIG. 6B). The lead 650 may include includes one or more conductors electrically coupling distal electrodes (not shown) of the lead 650 with proximal electrodes (or contacts 618), and as a result, the contacts 618 may be electrically coupled with the second set of member electrodes 696A, 696B, 696C, 696D.

FIG. 6B a cross-section of the lead taken though the second level (see 732 of FIG. 7B) of electrodes of FIG. 6A. A flexible member 640 is disposed over the lead 650 and electrically couples outer electrodes of the flexible member 640 to lead electrodes via inner electrodes and conductive traces of the flexible member. In the example shown, flexible member 640 has a first inner side 642 with three segmented electrodes 602A, 603A, 604A that generally align with lead segmented electrodes 620A, 620B, 620C. The flexible member 640 has a second outer side 652 that has a different configuration with a second set of member electrodes, for example segmented electrodes 603B, 604B. In some examples, the flexible member 640 may include conductive traces (not shown) that may electrically couple one or more of the member electrodes 602A, 603A, 604A with the second set member electrodes 603B, 604B.

The flexible member 640 reconfigures the electrodes, from a first configuration on the lead 650 to a second configuration of the second outer side 652 of the flexible member 640. In some examples, the flexible member 640 reconfigures the electrode configuration from a 1-3-3-1 configuration to a 2-2-2-2 configuration (FIGS. 7A and 7B). The first inner side 642 has a first set of member electrodes in a first electrode configuration, and in FIG. 6B a portion of the first set of member electrodes 602A, 603A, 604A are shown (i.e., electrodes at the second level).

In some examples, the first configuration of the first set of member electrodes (three segmented electrodes 602A, 603A, 604A) may generally correspond with the first configuration of the lead electrodes 620A, 620B, 620C where the first set of member electrodes generally correspond in position to a first configuration of lead electrodes. The first set of member electrodes may be disposed in contact with lead electrodes, and may thereby electrically connect the first set of member electrodes with lead electrodes 620A, 620B, 620C.

In one or more examples, the flexible member 640 includes a second outer side 652 and has a second set of member electrodes, where the second set of member electrodes are in a different configuration than the first set of member electrodes and allow for electrodes disposed along the lead at different levels to be re-configured into a different number of electrodes or different spacing of electrodes, different types of electrodes at the various electrode levels, different electrode positions, or different electrode sizes, for example, as described in FIGS. 3A, 3B. Electrodes 603B, 604B illustrate two of the second set of electrodes at a second level.

FIG. 6B shows a cross-section of flexible member 640 at a second level having a 1-3-3-1 configuration that matches a 1-3-3-1 configuration of a lead 650, such that each first inner side member electrode is in electrical contact with a corresponding electrode on the lead when the flexible member 640 is disposed over the lead. A second outer side 752 of flexible member 740 may have a 2-2-2-2 configuration with second outer side member electrodes, for example with two segmented electrodes 603B, 604B at a second level as shown in FIG. 6B. At the second level as shown in FIG. 6B, the second outer side 652 of the flexible member 640 also may have a pair of segmented electrodes 603B, 604B. Each of the segmented electrodes 602A, 603A, 604A of the first inner side 642 may be electrically coupled with the lead electrodes 620A, 620C, 620B, respectively. In some examples, the segmented electrodes 604B, 604B of the first inner side 642 may be electrically coupled with segmented electrodes 603B, 604B of the second side 652. In some examples, lead electrodes 620A and 620B may connect to outer electrodes 603B, 604B at the same axial level of the lead, and electrode 620C may electrically connect via a trace (not shown) to a segmented electrode at another level of the second set of electrodes. (See FIGS. 7A and 7B).

FIGS. 7A-10B illustrate various examples of flexible members in accordance with the disclosure herein. In some examples, the flexible member may comprise a flexible circuit, often referred to as a flex circuit. In some examples, the flexible member has a thickness of about 0.065 mm or less. In some examples, the flexible member has a thickness of about 0.065 mm. In one or more examples, the flexible member is defined in part by a width w. In some examples, the width w of the flexible member is substantially the same as a circumference perimeter value of the lead, where the perimeter value of the lead may be defined by the outer perimeter of the lead.

FIGS. 7A and 7B illustrate two sides of an example flexible member 740, where FIG. 7A illustrates a first inner side 742 of flexible member 740, and FIG. 7B illustrates a second outer side 752 of the flexible member 740. The flexible member 740 reconfigures the electrodes, from a first configuration (FIG. 7A) to a second configuration (FIG. 7B). The configurations shown in FIGS. 7A and 7B maintain the same overall number of electrodes, but provides a different configuration pattern.

In the example shown, the flexible member 740 reconfigures the electrode configuration from a 1-3-3-1 configuration (FIG. 7A) to a 2-2-2-2 configuration (FIG. 7B). The first inner side 742 has a first set of member electrodes 744 in a first electrode configuration. In some examples, the first configuration of the first set of member electrodes 744 generally corresponds with the first configuration of the lead electrodes where the first set of member electrodes 744 generally correspond in position to a first configuration of lead electrodes. In some examples, each of the first set of member electrodes 744 may be configured to be coupled to more than one electrode of the lead electrodes. In one or more examples, the flexible member 740 includes a second outer side 752 and has a second set of member electrodes 754, where the second set of member electrodes 754 are in a different configuration than the first set of member electrodes 744 and allow for electrodes disposed along the lead at different levels to be re-configured into a different number of electrodes or different spacing of electrodes, different types of electrodes at the various electrode levels, different electrode positions, or different electrode sizes, for example, as described in FIGS. 3A, 3B.

The second set of member electrodes 754 may be electrically coupled with the first set of member electrodes 744 by, for example, conductive traces 770. In some examples, the conductive traces 770 are printed on the flexible member. In some examples, the conductive traces 770 are disposed on and/or within the flexible member. In one or more examples, the first set of member electrodes 744 are printed electrodes. In one or more examples, the second set of member electrodes 754 are printed electrodes.

In one or more examples, electrodes 701A, 702A, 703A, 704A, 705A, 706A, 707A, 708A (collectively 701A-708A) of the first inner side 142 of the flexible member 740 are electrically coupled with electrodes 701B, 702B, 703B, 704B, 705B, 706B, 707B, 708B (collectively 701B-708B) of the second outer side 152 of the flexible member 740, respectively. In one or more examples electrodes 701A-708A are electrically coupled with electrodes 701B-708B via their respective traces 701C, 702C, 703C, 704C, 705C, 706C, 707C, 708C of the first inner side 742 and traces 701D, 702D, 703D, 704D, 705D, 706D, 707D, 708D of the second outer side 752. In some examples, the traces 701C, 702C, 703C, 704C, 705C, 706C, 707C, 708C of the first inner side 742 and traces 701D, 702D, 703D, 704D, 705D, 706D, 707D, 708D are disposed within one or more insulative layers between the first inner side and second outer side, and are electrically coupled within the insulative layers between the first inner side and second outer side. FIG. 7A shows an inner side of flexible member 740 having a 1-3-3-1 configuration that matches a 1-3-3-1 configuration of a lead (350A), such that each first inner side member electrode 744 is in electrical contact with a corresponding electrode on the lead when the flexible member 740 is disposed over the lead. FIG. 7B shows a second outer side 752 of flexible member 740 having a 2-2-2-2 configuration with second outer side member electrodes 754. Each second outer side member electrode 754 may be electrically coupled with a respective first inner side member electrode 744.

In FIG. 7B, respective traces 770D couple each ring electrode 790A, 794A (FIG. 7A) to one of a pair of segmented electrodes on the second outer side 752 of the flexible member 740. In some examples, respective traces 770C couple two of the segmented electrodes 782A in the second level on the inner side 742 to two segmented electrodes 796B on the second outer side 752, while another trace couples a third of the segmented electrodes 782A in the second level on the inner side 742 to one electrode of the pair of segmented electrodes on the second outer side at the first level. In some examples, at a first level 730, the second outer side of the flexible member may have a pair of segmented electrodes 701B, 702B, one (electrode 701B) coupled to the ring electrode of the lead at the first level and the other (electrode 702B) coupled to one of the trio of segmented electrodes of the lead at the second level. At the second level 732, the second outer side of the flexible member also may have a pair of segmented electrodes 703B, 704B, coupled to two (703A, 704A) of the trio of segmented electrodes of the lead at the second level on the first inner side 742.

At a third level 734, the second outer side of the flexible member also may have a pair of segmented electrodes 705B, 706B, coupled to two of the trio of segmented electrodes of the lead at the third level on the first inner side 742. At the fourth level 736, the second outer side of the flexible member also may have a pair of segmented electrodes 707B, 708B, where one of the segmented electrodes 707A may be coupled to one of the trio of segmented electrodes of the lead at the third level on the first inner side 742, and the other of the segmented electrodes 708B may be electrically coupled to the ring electrode of the lead at the fourth level on the first inner side 742.

Figure 8B:
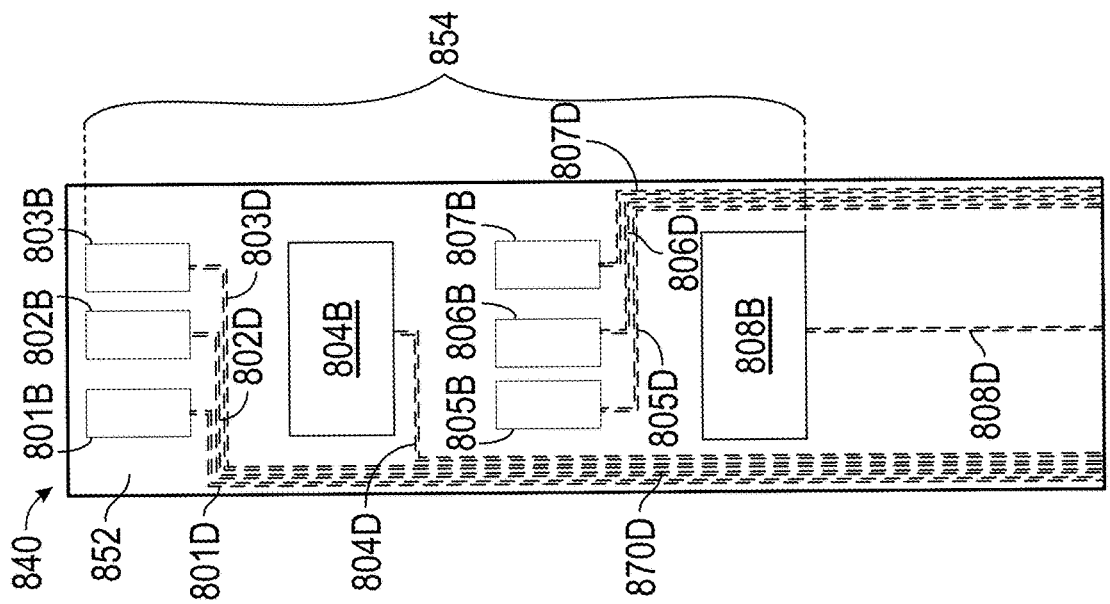
FIG. 8B is a conceptual diagram illustrating a second outer side of a flexible member in accordance with one or more techniques of this disclosure.
Figure 8A:
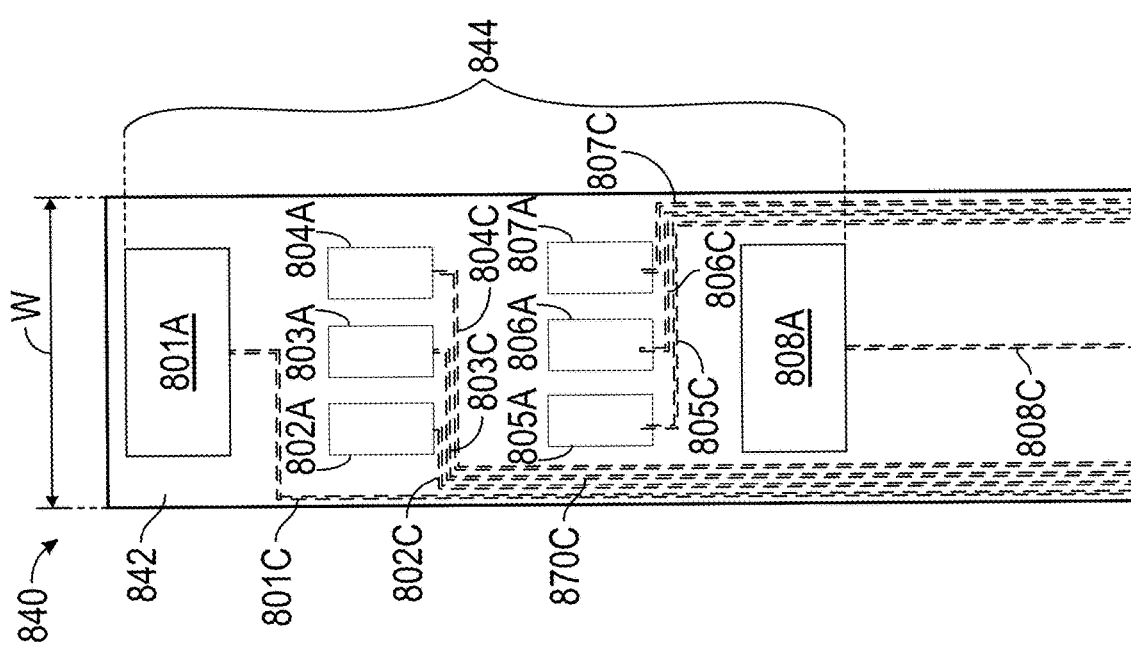
FIG. 8A is a conceptual diagram illustrating a first inner side of a flexible member in accordance with one or more techniques of this disclosure.

FIGS. 8A and 8B illustrate two sides of an example flexible member 840, where FIG. 8A illustrates a first inner side 842 of flexible member 840, and FIG. 8B illustrates a second outer side 852 of the flexible member 840. The flexible member 840 reconfigured the electrodes from a first configuration (FIG. 8A) to a second configuration (FIG. 7B). In the example shown, the flexible member 840 reconfigures the electrode configuration from a 1-3-3-1 configuration (FIG. 8A) to a (3-1-3-1) configuration (FIG. 8B). The first inner side 842 has a first set of member electrodes 844 in a first member configuration. In some examples, the first configuration of the first set of member electrodes 844 generally correspond with the first configuration of the lead electrodes where the first set of member electrodes 844 generally correspond in position to a first configuration of lead electrodes. In some examples, the first set of member electrodes 844 may be configured to be coupled to more than one electrode of the lead electrodes. In one or more examples, the flexible member 840 includes a second outer side 852 and has a second set of member electrodes 854, where the second set of member electrodes 854 are in a different configuration than the first set of member electrodes 844 and allow for electrodes disposed along the lead to be re-configured into a different number of electrodes or different spacing of electrodes, or different types of electrodes at the various electrode levels, for example as described in FIGS. 4A, 4B. The second set of member electrodes 854 may be electrically coupled with the first set of member electrodes 844 by, for example, conductive traces 870. In some examples, the conductive traces 870 are printed on the flexible member. In some examples, the conductive traces 870 are disposed on and/or within the flexible member. In one or more examples, the first set of member electrodes 844 are printed electrodes. In one or more examples, the second set of member electrodes 854 are printed electrodes.

In one or more examples, electrodes 801A, 802A, 803A, 804A, 805A, 806A, 807A, 808A (collectively 801A-808A) of the first inner side 842 of the flexible member 840 are electrically coupled with electrodes 801B, 802B, 803B, 804B, 805B, 806B, 807B, 808B (collectively 801B-808B) of the second outer side 852 of the flexible member 840, respectively. In one or more examples electrodes 801A-808A are electrically coupled with electrodes 801B-808B via their respective traces 801C, 802C, 803C, 804C, 805C, 806C, 807C, 808C of the first inner side 842 and traces 801D, 802D, 803D, 804D, 805D, 806D, 807D, 808D of the second outer side 852. FIG. 8A shows an inner side of flexible member 840 having a 1-3-3-1 configuration that matches a 1-3-3-1 configuration of a lead (450A), such that each first inner side member electrode 844 is in electrical contact with a corresponding electrode on the lead when the flexible member 840 is disposed over the lead (FIG. 4B). FIG. 8B shows an outer side 852 of flexible member 840 having a 3-1-3-1 configuration with second outer side member electrodes 854. Each second outer side member electrode 854 may be electrically coupled with a respective first inner side member electrode 844.

In FIG. 8B, respective traces 870D couple each ring electrode 801A, 808A (FIG. 8A) to one of three of segmented electrodes on the second outer side 852 of the flexible member 840. In some examples, respective traces 870D couple two of the three segmented electrodes 802A, 803A in the second level on the inner side 842 to two segmented electrodes 802B, 803B on the second outer side 852 in the first level, while another trace couples a third of the segmented electrodes 804A in the second level on the inner side 842 to ring electrode 804B on the outer side at the first level. In some examples, at a first level, the second outer side of the flexible member 940 may have three segmented electrodes 801B, 802B, 803B coupled to the ring electrode of the lead at the first level and the others (electrode 802B, 803B) coupled to two of the trio of segmented electrodes of the lead at the second level. The second outer side may have a ring electrode 804B coupled to a third of the three segmented electrode at the second level of the lead. At the third level, the second outer side 852 of the flexible member 840 also may have three segmented electrodes 805B, 806B, 807B coupled to three (805A, 806A, 807A) of the trio of segmented electrodes of the lead at the third level on the first inner side 842.

The second outer side 852 of the flexible member 840 also may have a second ring electrode 808B coupled to a second ring electrode of the lead on the first inner side 842.

The configurations shown in FIGS. 8A and 8B maintain the same overall number of electrodes, but provide a different configuration pattern of the electrodes on the lead.

FIGS. 9A and 9B illustrate two sides of an example flexible member 940, where FIG. 9A illustrates a first inner side 942 of flexible member 940, and FIG. 9B illustrates a second outer side 952 of the flexible member 940. The first inner side 942 has a first set of member electrodes 944 in a first member configuration. In some examples, the first configuration of the first set of member electrodes 944 generally correspond with the first configuration of the lead electrodes where the first set of member electrodes 944 generally correspond in position to a first configuration of lead electrodes. In some examples, the first set of member electrodes 944 may be configured to be coupled to more than one electrode of the lead electrodes. In one or more examples, the flexible member 940 includes a second outer side 952 and has a second set of member electrodes 954, where the second set of member electrodes 954 are in a different configuration than the first set of member electrodes 944 and allow for electrodes disposed along the lead to be re-configured into a different number of electrodes or different spacing of electrodes, or different types of electrodes at the various electrode levels. For example, FIG. 9A illustrates a first longitudinal spacing of the first set of member electrodes 944 and FIG. 9B illustrates a second longitudinal spacing of the second set of member electrodes 954, where in one example the second set of member electrodes 954 are spaced longitudinally further apart than the first set of member electrodes 944. In some examples, the second set of member electrodes 954 are spaced longitudinally closer together than the first set of member electrodes 944.

The second set of member electrodes 954 may be electrically coupled with the first set of member electrodes 944 by, for example, conductive traces 970. In some examples, the conductive traces 970 are printed on the flexible member. In some examples, the conductive traces 970 are disposed on and/or within the flexible member. In one or more examples, the first set of member electrodes 944 are printed electrodes. In one or more examples, the second set of member electrodes 954 are printed electrodes.

In one or more examples, electrodes 901A, 902A, 903A, 904A, 905A, 906A, 907A, 908A (collectively 901A-908A) of the first inner side 942 of the flexible member 940 are electrically coupled with electrodes 901B, 902B, 903B, 904B, 905B, 906B, 907B, 908B (collectively 901B-908B) of the second outer side 952 of the flexible member 940, respectively. In one or more examples electrodes 901A-908A are electrically coupled with electrodes 901B-908B via their respective traces 901C, 902C, 903C, 904C, 905C, 906C, 907C, 908C of the first inner side 942 and traces 901D, 902D, 903D, 904D, 905D, 906D, 907D, 908D of the second outer side 952.

FIG. 9A shows an inner side of flexible member 940 having a 1-3-3-1 configuration that matches a 1-3-3-1 configuration of a lead, such that each first inner side member electrode 944 is in electrical contact with a corresponding electrode on the lead when the flexible member 940 is disposed over the lead. FIG. 9B shows a second outer side 952 of flexible member 940 also having a 1-3-3-1 configuration with second outer side member electrodes 954, however the longitudinal spacing of the electrodes for the outer side 952 is different than the inner side 942. In some examples, the second outer side member electrodes 954 are spaced further longitudinally apart from each other than the inner side electrodes 944. Each second outer side member electrode 954 may be electrically coupled with a respective first inner side member electrode 944.

The configurations shown in FIGS. 9A and 9B maintain the same overall number of electrodes, but provide a different longitudinal spacing of the electrodes on the lead. In some examples, the flexible member 940 may provide different axial spacing on the second outer side than the axial spacing of the electrodes on the lead.

Figure 10B:
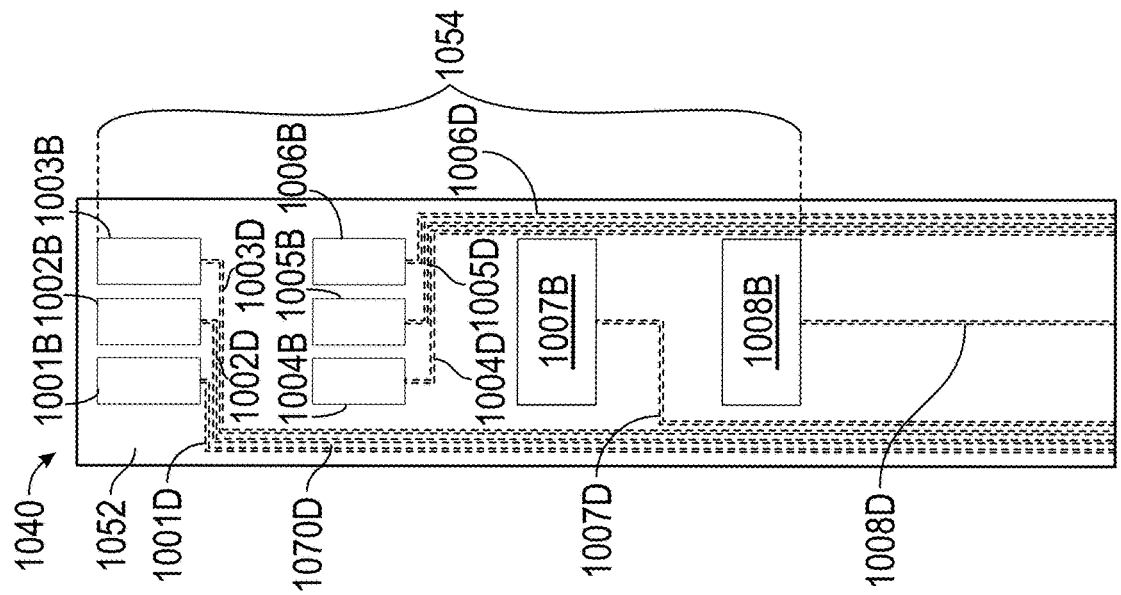
FIG. 10B is a conceptual diagram illustrating a second outer side of a flexible member in accordance with one or more techniques of this disclosure.
Figure 10A:
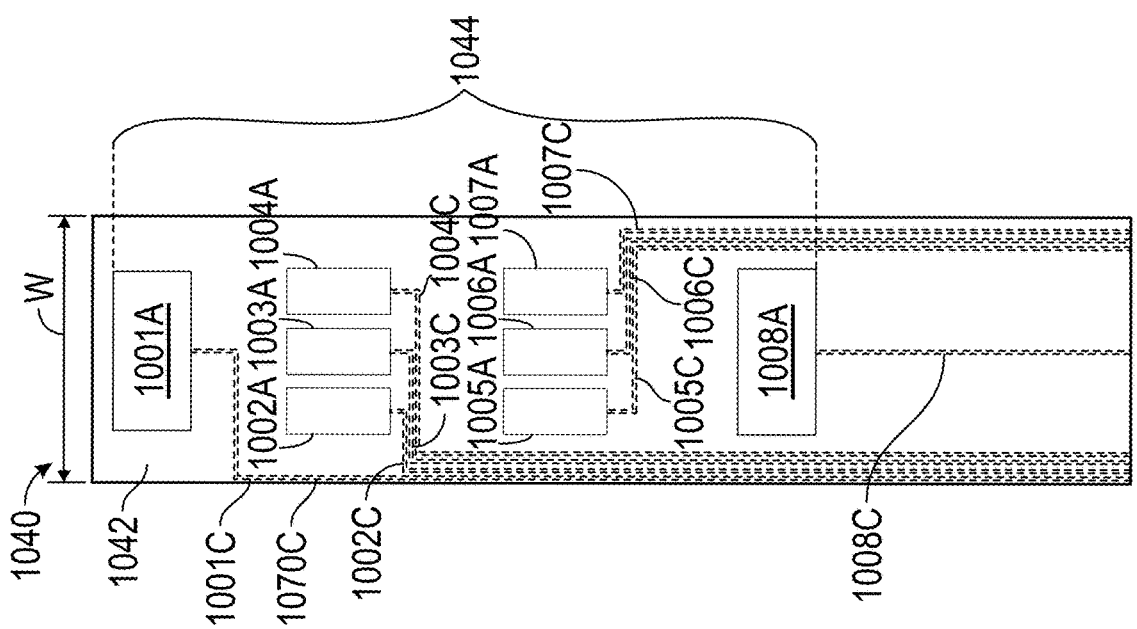
FIG. 10A is a conceptual diagram illustrating a first inner side of a flexible member in accordance with one or more techniques of this disclosure.

FIGS. 10A and 10B illustrate two sides of an example flexible member 1040, where FIG. 10A illustrates a first inner side 1042 of flexible member 1040, and FIG. 10B illustrates a second outer side 1052 of the flexible member 1040. The flexible member 1040 reconfigured the electrodes from a first configuration (FIG. 10A) to a second configuration (FIG. 10B). In the example shown, the flexible member 1040 reconfigures the electrode configuration from a 1-3-3-1 configuration (FIG. 10A) to a (3-3-1-1) configuration (FIG. 10B). The first inner side 1042 has a first set of member electrodes 1044 in a first member configuration. In some examples, the first configuration of the first set of member electrodes 1044 generally correspond with the first configuration of the lead electrodes where the first set of member electrodes 1044 generally correspond in position to a first configuration of lead electrodes. In some examples, the first set of member electrodes 1044 may be configured to be coupled to more than one electrode of the lead electrodes. In one or more examples, the flexible member 1040 includes a second outer side 1052 and has a second set of member electrodes 1054, where the second set of member electrodes 1054 are in a different configuration than the first set of member electrodes 1044 and allow for electrodes disposed along the lead to be re-configured into a different number of electrodes or different spacing of electrodes, or different types of electrodes at the various electrode levels, for example as described for FIGS. 5A, 5B. The second set of member electrodes 1054 may be electrically coupled with the first set of member electrodes 1044 by, for example, conductive traces 1070. In some examples, the conductive traces 1070 are printed on the flexible member. In some examples, the conductive traces 1070 are disposed on and/or within the flexible member. In one or more examples, the first set of member electrodes 1044 are printed electrodes. In one or more examples, the second set of member electrodes 1054 are printed electrodes.

In one or more examples, electrodes 1001A, 1002A, 1003A, 1004A, 1005A, 1006A, 1007A, 1008A (collectively 1001A-1008A) of the first inner side 1042 of the flexible member 1040 are electrically coupled with electrodes 1001B, 1002B, 1003B, 1004B, 1005B, 1006B, 1007B, 1008B (collectively 1001B-1008B) of the second outer side 1052 of the flexible member 1040, respectively. In one or more examples electrodes 1001A-1008A are electrically coupled with electrodes 1001B-1008B via their respective traces 1001C, 1002C, 1003C, 1004C, 1005C, 1006C, 1007C, 1008C of the first inner side 1042 and traces 1001D, 1002D, 1003D, 1004D, 1005D, 1006D, 1007D, 1008D of the second outer side 1052. FIG. 10A shows an inner side of flexible member 1040 having a 1-3-3-1 configuration that matches a 1-3-3-1 configuration of a lead (550A), such that each first inner side member electrode 1044 is in electrical contact with a corresponding electrode on the lead when the flexible member 1040 is disposed over the lead (FIG. 5B). FIG. 10B shows a second outer side 1052 of flexible member 1040 having a 3-3-1-1 configuration with second outer side member electrodes 1054. Each second outer side member electrode 1054 may be electrically coupled with a respective first inner side member electrode 1044.

In FIG. 10B, trace 1001C may couple ring electrode 1001A (FIG. 10A) to trace 1001D, and to one (1001B) of three of segmented electrodes on the second outer side 1052 of the flexible member 1040. In some examples, respective traces 1070C, or specifically 1002C, 1003C may couple two of the three segmented electrodes 1002A, 1003A in the second level on the inner side 1042 to two segmented electrodes 1002B, 1003B on the second outer side 1052 in the first level via traces 1002D, 1003D. In some examples, trace 10004C may couple one of the three segmented electrodes 1004A in the second level on the inner side 1042 to one of the three segmented electrodes at the second level of the second outer side 1052 via trace 1004D.

In some examples, respective traces 1070C, or specifically 1005C, 1006C may couple two of the three segmented electrodes 1005A, 1006A in the third level on the inner side 1042 to two segmented electrodes 1005B, 1006B on the second outer side 1052 in the second level via traces 1005D, 1006D. In some examples, trace 1007C may couple one (1007A) of three segmented electrodes in the third level on the inner side 1042 to a ring electrode 1008B on the second outer side 1052 of the flexible member via trace 1008D. In come examples, trace 1008C may couple a second ring electrode 1008A on the first inner side 1042 to a second ring electrode 1008B on the second outer side 1052 via trace 1008D.

The configurations shown in FIGS. 10A and 10B maintain the same overall number of electrodes, but provide a different configuration pattern of the electrodes on the lead.

Figure 11:
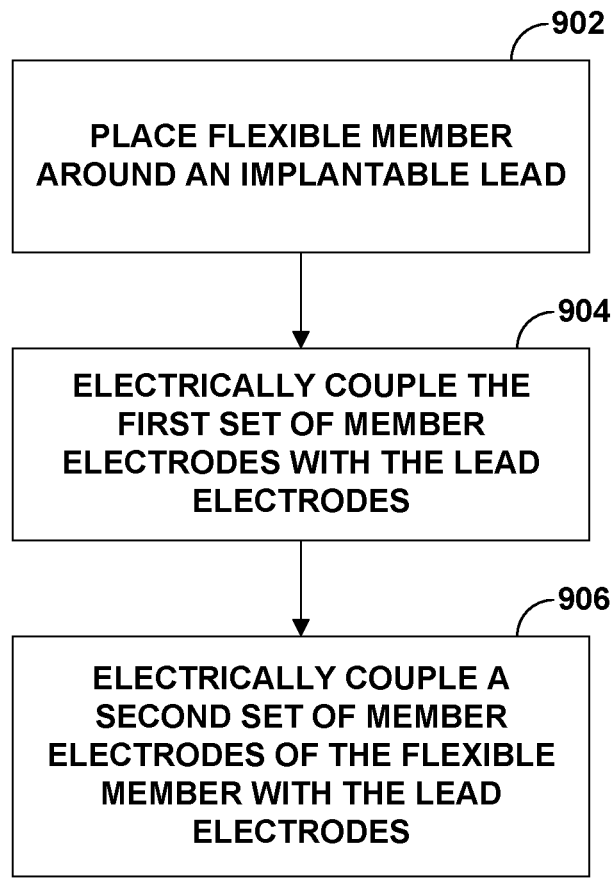
FIG. 11 is a flow diagram of an example technique in accordance with one or more techniques of this disclosure.

FIG. 11 is a flow diagram of an example technique for the disclosures herein. In one or more examples, the technique includes placing a flexible member around an implantable lead (902). In some examples, the flexible member is disposed over the lead. In one or more examples, the flexible member is wrapped around the lead. In one more examples, the flexible member is coiled around the lead. In some examples, the flexible member is a tube disposed over the lead. The flexible member, in some examples, may be secured to the lead. For example, the flexible member may be adhered to the lead with adhesive, or mechanically fixated to the lead, or heat shrunk over the lead. In some examples, solder reflow may be used to fuse lead electrodes and inner member electrodes together.

In some examples, the implantable lead comprising multiple levels of lead electrodes in a first segmented electrode configuration. For the first configuration, at least one level of the lead electrodes may include segmented electrodes. The flexible member may include a first inner side and a first set of member electrodes, at least some of the first set of member electrodes configured to be positioned to electrically contact corresponding lead electrodes of the first segmented electrode configuration. The flexible member may further include a second outer side and a second set of member electrodes in a second segmented electrode configuration which is different than the first segmented electrode configuration. At least some of the second set of member electrodes may be electrically coupled to corresponding member electrodes of the first set of member electrodes.

At 904, the first set of member electrodes of the flexible member may be coupled with the lead electrodes. For example, the first set of member electrodes may be disposed in contact with the lead electrodes. In some examples, the first set of member electrodes may be aligned with the lead electrodes. In some examples, an electrically conductive material may be placed between the first set of member electrodes and the lead electrodes. In one or more examples, the second set of member electrodes are electrically coupled with the lead electrodes (906). In some examples, electrically coupling the second set of member electrodes with the lead electrodes occurs coincident with electrically coupling the first set of member electrodes with the lead electrodes. wherein placing the flexible member around the implantable lead includes electrically coupling one or more of the first set of member electrodes with the lead electrodes and electrically coupling the lead electrodes with the second set of member electrodes.

The following examples are described herein.

Example 1. A medical system for electrical stimulation therapy comprising: an implantable lead with multiple levels of lead electrodes in a first segmented electrode configuration, at least one level of the lead electrodes comprising segmented electrodes, the implantable lead extending from a proximal end to a distal end; and a flexible member configured to be disposed over the first electrode segmented electrode configuration, the flexible member having a first inner side and a first set of member electrodes, at least some of the first set of member electrodes configured to be positioned to electrically contact corresponding lead electrodes of the first segmented electrode configuration, the flexible member having a second outer side and a second set of member electrodes in a second segmented electrode configuration which is different than the first segmented electrode configuration, at least some of the second set of member electrodes electrically coupled to corresponding member electrodes of the first set of member electrodes.

Example 2. The medical system of example 1, wherein the flexible member comprises a flexible circuit.

Example 3. The medical system of any of examples 1 or 2, wherein at least one of the first set of member electrodes or the second set of member electrodes comprise printed electrodes.

Example 4. The medical system of any of examples 1-3, wherein the flexible member has a thickness of about 0.065 mm or less.

Example 5. The medical system of any of examples 1-4, wherein at least one of the lead electrodes is a ring electrode.

Example 6. The medical system of any of examples 1-5, wherein the first segmented electrode configuration has more electrodes than the second segmented electrode configuration.

Example 7. The medical system of any of examples 1-6, wherein the implantable lead has a circumference value and the flexible member has a width, wherein the width is substantially same as the circumference value.

Example 8. The medical system of any of examples 1-7, wherein the first segmented electrode configuration has a first longitudinal spacing between one or more of the lead electrodes and the second segmented electrode configuration has a second longitudinal spacing between one or more of the second set of member electrodes, and the first longitudinal spacing is different than the second longitudinal spacing.

Example 9. The medical system of any of examples 1-8, wherein the first segmented electrode configuration is a 1-3-3-1 configuration comprising a first ring electrode, a first level of three segmented electrodes, a second level of three segmented electrodes and a second ring electrode, and the second electrode configuration is a 2-2-2-2 configuration where each level has two segmented electrodes.

Example 10. The medical system of any of examples 1-8, wherein the first segmented electrode configuration is a 1-3-3-1 configuration comprising a first ring electrode, a first level of three segmented electrodes, a second level of three segmented electrodes and a second ring electrode, and the second electrode configuration is a 3-1-3-1 configuration comprising a member first level of three segmented electrodes, a member first ring electrode, a member second level of three segmented electrodes and a member second ring electrode.

Example 11. The medical system of any of examples 1-9, wherein the first segmented electrode configuration is a 1-3-3-1 configuration comprising a first ring electrode, a first level of three segmented electrodes, a second level of three segmented electrodes and a second ring electrode, and the second electrode configuration is a 3-3-1-1 configuration comprising a member first level of three segmented electrodes, a member second level of three segmented electrodes, a member first ring electrode, and a member second ring electrode.

Example 12. The medical system of any of examples 1-11, wherein the flexible member is disposed around at least a portion of the implantable lead proximate the distal end of the implantable lead such that the first inner side forms an inner surface of the flexible member and the second outer side forms an outer surface of the flexible member.

Example 13. The medical system of example 12, wherein the flexible member is coiled around at least a portion of the implantable lead.

Example 14. The medical system of any of examples 12-13, wherein the flexible member disposed over the first segmented electrode configuration, the flexible member wrapped around at least a portion of the implantable lead proximate a distal end of the lead and the first set of member electrodes of the first segmented electrode configuration are electrically coupled with the lead electrodes.

Example 15. The medical system of example 14, wherein the implantable lead has one or more proximal electrodes near the proximal end, the proximal electrodes electrically coupled to the lead electrodes at a distal end of lead, and the proximal electrodes coupled via the flexible member to the second set of member electrodes.

Example 16. The medical system of any of examples 1-15, further comprising a stimulation generator electrically coupled to at least some of the lead electrodes to deliver stimulation.

Example 17. The medical system of any of examples 1-16, wherein the flexible member includes one or more conductive traces on or within the flexible member, where the conductive traces electrically couple the first set of member electrodes to the second set of member electrodes.

Example 18. The medical device of any of examples 1-16, further comprising sensing circuitry coupled to at least some of the lead electrodes configured to sense electrical signals.

Example 19. The medical system of any of examples 1-8, wherein the first segmented electrode configuration is a 1-3-3-1 configuration comprising a first ring electrode, a first level of three segmented electrodes, a second level of three segmented electrodes and a second ring electrode, and the second electrode configuration is a 2-3-2-2 configuration where each level has two segmented electrodes at a first level, second level, third level, fourth level, wherein the first ring electrode is electrically coupled to one or more of a pair of segmented electrodes at the first level, one or more of the first level of three segmented electrodes of the first segmented electrode configuration is electrically coupled with one or more of a pair of segmented electrodes at the second level of the second electrode configuration, two of the segmented electrodes of the first level of three segmented electrodes are electrically coupled with two segmented electrodes at the second level of the second electrode configuration, two of the segmented electrodes of the second level of three segmented electrodes are electrically coupled with two segmented electrodes at the third level of the second electrode configuration, one or the segmented electrodes of the second level of three segmented electrodes are electrically coupled with one or more of a pair of segmented electrodes at the fourth level of the second electrode configuration, and the second ring electrode electrically coupled with one or more of a pair of segmented electrodes at the fourth level of the second electrode configuration.

Example 20. A method comprising: placing a flexible member around an implantable lead, the implantable lead comprising multiple levels of lead electrodes in a first segmented electrode configuration, at least one level of the lead electrodes comprising segmented electrodes, the implantable lead extending from a proximal end to a distal end, the flexible member having a first inner side and a first set of member electrodes, at least some of the first set of member electrodes configured to be positioned to electrically contact corresponding lead electrodes of the first segmented electrode configuration, the flexible member having a second outer side and a second set of member electrodes in a second segmented electrode configuration which is different than the first segmented electrode configuration, at least some of the second set of member electrodes electrically coupled to corresponding member electrodes of the first set of member electrodes; wherein placing the flexible member around the implantable lead includes electrically coupling one or more of the first set of member electrodes with the lead electrodes and electrically coupling the lead electrodes with the second set of member electrodes.

Example 21. The method of example 20, wherein placing the flexible member around the implantable lead includes coiling the flexible member around the implantable lead.

Example 22. The method of example 20, further comprising adhering the flexible member with the implantable lead.

Example 23. The method of any of examples 20-22, further comprising connecting the implantable lead to at least one of electrical stimulation generation circuitry or sensing circuitry.

Example 24. A medical system for electrical stimulation therapy comprising: an implantable lead with multiple levels of lead electrodes in a first segmented electrode configuration, at least one level of the lead electrodes comprising segmented electrodes, the implantable lead extending from a proximal end to a distal end; a flexible member configured to be disposed over the first electrode segmented electrode configuration, the flexible member having a first inner side and a first set of member electrodes, at least some of the first set of member electrodes configured to be positioned to electrically contact corresponding lead electrodes of the first segmented electrode configuration, wherein the flexible member having a second outer side and a second set of member electrodes in a second segmented electrode configuration which is different than the first segmented electrode configuration, at least some of the second set of member electrodes electrically coupled to corresponding member electrodes of the first set of member electrodes; and an implantable medical device comprising: a stimulation generator electrically coupled to at least some of the lead electrodes and configured to deliver stimulation; and sensing circuitry coupled to at least some of the lead electrodes and configured to sense electrical signals.

The above features and techniques are examples. Any suitable techniques may be used to fabricate the structures described herein and may vary based on the particular materials employed for the respective components.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided.

These examples may be combined in any permutation or combination. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

Various aspects of the disclosure have been described. These and other aspects are within the scope of the following claims.

What is claimed is:

1. A medical system for electrical stimulation therapy, the medical system comprising:
   an implantable lead with multiple axial levels of lead electrodes in a first segmented electrode configuration, at least one axial level of the multiple axial levels comprising multiple electrodes located at different positions around a perimeter of the implantable lead, the implantable lead extending from a proximal end to a distal end; and
   a flexible member defining an inner side and an outer side and comprising a first set of member electrodes on the inner side and a second set of member electrodes on the outer side in a second segmented electrode configuration, the first set of member electrodes being different than the second set of member electrodes, wherein:
   the flexible member is configured to be disposed over the first segmented electrode configuration and at least a portion of the implantable lead,
   at least some member electrodes of the first set of member electrodes are configured to be positioned to electrically contact corresponding lead electrodes of the first segmented electrode configuration of the implantable lead, and
   at least some member electrodes of the second set of member electrodes are electrically coupled to corresponding member electrodes of the first set of member electrodes.

2. The medical system of claim 1, wherein the flexible member comprises a flexible circuit.

3. The medical system of claim 1, wherein at least one of the first set of member electrodes or the second set of member electrodes comprise printed electrodes.

4. The medical system of claim 1, wherein the flexible member has a thickness of about 0.065 mm or less.

5. The medical system of claim 1, wherein at least one of the lead electrodes is a ring electrode.

6. The medical system of claim 1, wherein the first segmented electrode configuration has more electrodes than the second segmented electrode configuration.

7. The medical system of claim 1, wherein the implantable lead has a circumference value and the flexible member has a width, wherein the width is substantially the same as the circumference value such that the inner side of the flexible member is configured to contact the implantable lead when the flexible member is disposed over the implantable lead.

8. The medical system of claim 1, wherein the first segmented electrode configuration has a first longitudinal spacing between one or more of the lead electrodes and the second segmented electrode configuration has a second longitudinal spacing between one or more of the second set of member electrodes, and wherein the first longitudinal spacing is different than the second longitudinal spacing.

9. The medical system of claim 1, wherein the first segmented electrode configuration is a 1-3-3-1 configuration comprising a first ring electrode, a first level of three segmented electrodes, a second level of three segmented electrodes and a second ring electrode, and the second electrode configuration is a 2-2-2-2 configuration where each level has two segmented electrodes.

10. The medical system of claim 1, wherein the first segmented electrode configuration is a 1-3-3-1 configuration comprising a first ring electrode, a first level of three segmented electrodes, a second level of three segmented electrodes and a second ring electrode, and the second electrode configuration is a 3-1-3-1 configuration comprising a member first level of three segmented electrodes, a member first ring electrode, a member second level of three segmented electrodes and a member second ring electrode.

11. The medical system of claim 1, wherein the first segmented electrode configuration is a 1-3-3-1 configuration comprising a first ring electrode, a first level of three segmented electrodes, a second level of three segmented electrodes and a second ring electrode, and the second electrode configuration is a 3-3-1-1 configuration comprising a member first level of three segmented electrodes, a member second level of three segmented electrodes, a member first ring electrode, and a member second ring electrode.

12. The medical system of claim 1, wherein the flexible member is disposed around at least a portion of the implantable lead proximate the distal end of the implantable lead such that the inner side forms an inner surface of the flexible member and the outer side forms an outer surface of the flexible member, and wherein the inner side contacts the implantable lead.

13. The medical system of claim 12, wherein the flexible member is coiled around at least a portion of the implantable lead.

14. The medical system of claim 12, wherein the flexible member is disposed over the first segmented electrode configuration, the flexible member is wrapped around at least a portion of the implantable lead proximate a distal end of the lead and the first set of member electrodes are electrically coupled with the lead electrodes.

15. The medical system of claim 1, further comprising a stimulation generator electrically coupled to at least some lead electrodes of the lead electrodes and configured to deliver stimulation.

16. The medical system of claim 1, wherein the flexible member includes one or more conductive traces on or within the flexible member, where the conductive traces electrically couple the first set of member electrodes to the second set of member electrodes.

17. The medical system of claim 1, further comprising sensing circuitry coupled to at least some electrodes of the lead electrodes configured to sense electrical signals.

18. A method comprising:
placing a flexible member around an implantable lead, the implantable lead comprising multiple axial levels of lead electrodes in a first segmented electrode configuration, at least one axial level of the multiple axial levels comprising electrodes located at different positions around a perimeter of the implantable lead, the implantable lead extending from a proximal end to a distal end, the flexible member defining an inner side and an outer side and comprising a first set of member electrodes on the inner side and a second set of member electrodes on the outer side in a second segmented electrode configuration, the first set of member electrodes being different than the second set of member electrodes,
wherein at least some member electrodes of the first set of member electrodes are configured to be positioned to electrically contact corresponding lead electrodes of the first segmented electrode configuration of the implantable lead,
wherein at least some member electrodes of the second set of member electrodes are electrically coupled to corresponding member electrodes of the first set of member electrodes, and
wherein placing the flexible member around the implantable lead includes electrically coupling one or more member electrodes of the first set of member electrodes with the lead electrodes and electrically coupling the lead electrodes with the second set of member electrodes.

19. The method of claim 18, wherein placing the flexible member around the implantable lead includes coiling the flexible member around the implantable lead.

20. The method of claim 18, further comprising adhering the flexible member with the implantable lead.

21. The method of claim 18, further comprising connecting the implantable lead to at least one of electrical stimulation generation circuitry or sensing circuitry.

22. A medical system for electrical stimulation therapy comprising:
an implantable lead with multiple axial levels of lead electrodes in a first segmented electrode configuration, at least one axial level of the multiple axial levels comprising multiple electrodes located at different positions around a perimeter of the implantable lead, the implantable lead extending from a proximal end to a distal end; and
a flexible member defining an inner side and an outer side and comprising a first set of member electrodes on the inner side and a second set of member electrodes on the outer side in a second segmented electrode configuration, the first set of member electrodes being different than the second set of member electrodes, wherein:
the flexible member is configured to be disposed over the first segmented electrode configuration and at least a portion of the implantable lead,
at least some member electrodes of the first set of member electrodes are configured to be positioned to electrically contact corresponding lead electrodes of the first segmented electrode configuration of the implantable lead,
wherein, at least some member electrodes of the second set of member electrodes are electrically coupled to corresponding member electrodes of the first set of member electrodes; and
an implantable medical device comprising:
a stimulation generator configured to be electrically coupled to at least some of the lead electrodes and configured to deliver stimulation; and
sensing circuitry configured to be coupled to at least some of the lead electrodes and configured to sense electrical signals.

\* \* \* \* \*